United States Patent [19]

Weaver et al.

[11] Patent Number: 5,086,161

[45] Date of Patent: Feb. 4, 1992

[54] NOVEL METHINE COMPOUNDS, POLYMERS CONTAINING THEM AND FORMED ARTICLES THEREFROM

[75] Inventors: Max A. Weaver; Wayne P. Pruett, both of Kingsport; Samuel D. Hilbert, Jonesborough, all of Tenn.

[73] Assignee: Eastman Kodak Company, Rochester, N.Y.

[21] Appl. No.: 701,401

[22] Filed: May 6, 1991

Related U.S. Application Data

[62] Division of Ser. No. 454,087, Dec. 20, 1989, which is a division of Ser. No. 182,633, Apr. 18, 1988, Pat. No. 4,958,043.

[51] Int. Cl.[5] ............................................. C08G 63/20
[52] U.S. Cl. ...................... 528/288; 528/272; 528/289; 528/290; 528/291; 528/292; 528/294; 528/295; 528/298; 528/299; 528/300; 528/302; 528/303; 528/307; 528/308.6; 528/367; 528/370; 528/373; 528/422; 528/425
[58] Field of Search ............... 528/272, 288, 289, 290, 528/291, 292, 294, 295, 298, 299, 300, 302, 303, 304, 308.6, 367, 370, 373, 422, 425

[56] References Cited

U.S. PATENT DOCUMENTS

| | | | |
|---|---|---|---|
| 3,634,320 | 1/1972 | Metaner et al. | 524/287 |
| 4,338,247 | 7/1982 | Zannucci et al. | 528/307 |

FOREIGN PATENT DOCUMENTS

| | | |
|---|---|---|
| 1568693 | 3/1970 | Fed. Rep. of Germany . |
| 86/04903 | 8/1986 | PCT Int'l Appl. . |
| 86/04904 | 8/1986 | PCT Int'l Appl. . |
| 87-01121 | 2/1987 | PCT Int'l Appl. . |
| 88/02384 | 4/1988 | PCT Int'l Appl. . |

OTHER PUBLICATIONS

Plastics Additives Handbook, edited by R. Gächter and H. Müller, pp. 128-134 (Hanser Publishers, 1985).

*Primary Examiner*—Maurice J. Welsh
*Assistant Examiner*—S. A. Acquah
*Attorney, Agent, or Firm*—Bernard J. Graves, Jr.; William P. Heath, Jr.

[57] ABSTRACT

A composition useful for incorporation into polymer compositions employed for food packaging or the like comprising a bis- or tris-methine compound having the structural formula

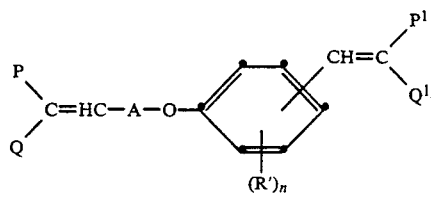

wherein
A is selected from the radicals

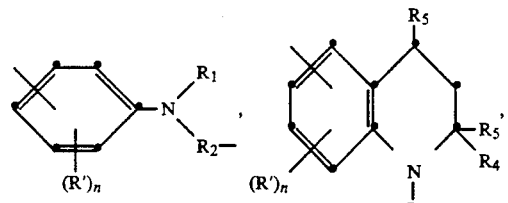

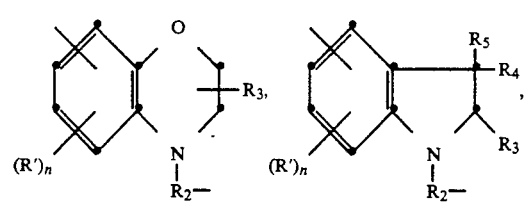

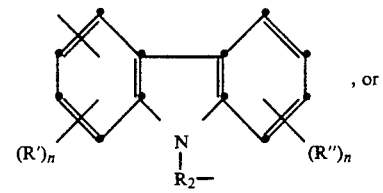

, or

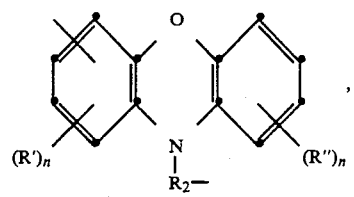

wherein
R' and R" are each selected from chlorine, bromine, fluorine, alkyl, alkoxy, aryl, aryloxy and arylthio;
each n is independently 0, 1, 2;
$R_1$ is selected from a large variety of radicals such as cycloalkyl, phenyl, and straight or branched alkyl which may be subsituted;
$R_2$ is alkylene or the like;
$R_3$, $R_4$, and $R_5$ are each selected from hydrogen and alkyl; and
P and Q and $P^1$ and $Q^1$ are selected from cyano, carbalkoxy, carbaryloxy, carbaralkyloxy, or the like.

The invention compositions are especially useful in combination with molding or fiber-grade condensation polymer; most preferably such polymer having compolymerized therein a total of from 1.0 to about 100,000 ppm, of the reactant residue moieties of one or more of such bis- or tris-methine compounds.

6 Claims, No Drawings

NOVEL METHINE COMPOUNDS, POLYMERS CONTAINING THEM AND FORMED ARTICLES THEREFROM

This is a divisional application of copending application Ser. No. 07/454,087 filed on Dec. 20, 1989, which is a divisional application of Ser. No. 07/182,633 filed on Apr. 18, 1988 now U.S. Pat. No. 4,958,043.

TECHNICAL FIELD

This invention concerns novel methine compounds, polymer blends containing such methine compounds, and condensation polymers containing the same copolymerized therein, including linear polyester, unsaturated polyester, and polycarbonate types. The present compounds, bis- and tris-methines, which can optionally be copolymerized (condensed) into the polymer chain, impart UV screening thereto and also colors ranging from light to dark yellow. It is particularly noted that this unique property of the present compounds affords much easier compounding of the additive and polymer in that the sublimation, volatility, compatability and the like properties of multiple additives normally required for attaining both UV screening and coloring, are not such onerous considerations in the use of only one compound as in accordance with the present invention. The bis- and tris-methine moieties are thermally stable and nonsublimable at the polymer processing (includes preparation) temperatures, are nonextractable therefrom, especially when copolymerized into the polymer chain, and absorb radiation over the entire harmful UV wavelength, thus rendering the polymers particularly suitable for use as beverage bottles and food, pharmaceutical and cosmetic containers. The bis- and tris-methine reactant residues or moieties are useful in total concentrations, given herein in parts per million (ppm), ranging from about 1.0 to about 100,000, preferably 2.0 to about 1,500 ppm, and most preferably from about 100 to about 800 ppm (parts by weight of moiety per million parts by weight of final polymer).

BACKGROUND ART

Heretofore, various UV absorbers such as the benzophenones, benzotriazoles and resorcinol monobenzoates have been incorporated into polymers as discussed in Plastics Additives Handbook, Hanser Publishers, Library of Congress Catalog No. 83-062289, pp 128-134, for use in absorbing or screening deleterious radiation. These additives function well to screen radiation in the range of from about 300 to about 350 nm; however, this range is not adequate to protect the contents of food packaging employing these polymers. Moreover, when these compounds are added to polyesters, they are extractable by solvents which may be present in food packaged with the polymers. Such solvents would include typical food acids, alcohols and the like. Furthermore, these compounds are not, in general, stable under the polyester manufacturing and processing conditions and often produce objectionable yellow discoloration in food packaging. Also, the various copolyesters such as disclosed in U.S. Pat. No. 4,338,247, while having essentially nonextractable UV absorbers, are not suitable for food packaging in that the absorbers transmit harmful radiation and are not designed to protect food.

U.S. Pat. No. 3,634,320 discloses compounds somewhat similar to those disclosed herein for mixing into various polymers for U.V. absorption, however, copolymerization is not involved and the wavelength of maximum absorption for these compounds are not sufficiently high to protect food.

DISCLOSURE OF INVENTION

The present invention is defined in its broad embodiment as a composition comprising bis- or tris-methine moieties having the structural formula

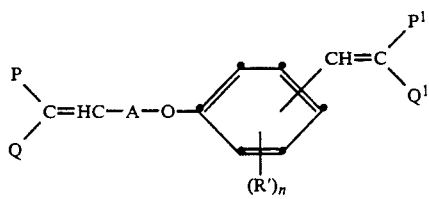

wherein
A is selected from the radicals

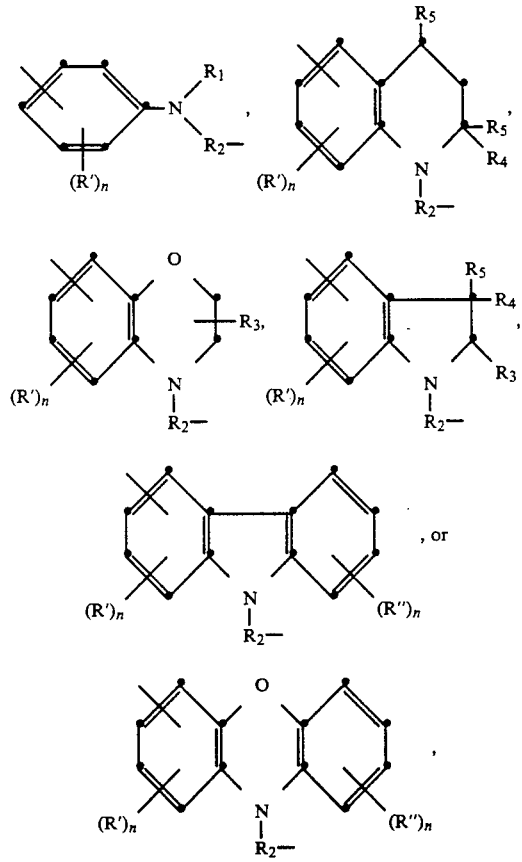

wherein
R' and R'' are each selected from chlorine, bromine, fluorine, alkyl, alkoxy, aryl, aryloxy, and arylthio;
each n is independently 0, 1, 2;
$R_1$ is selected from cycloalkyl; cycloalkyl substituted with one or two of alkyl, —OH, alkoxy, halogen, or hydroxy substituted alkyl; phenyl; phenyl substituted with alkyl, alkoxy, halogen, alkanoylamino, carboxy, cyano, or alkoxycarbonyl; straight or branched lower alkenyl; straight or branched alkyl of 1–8 carbons and such alkyl substituted with the following: hydroxy; halogen; cyano; succinimido; hydroxysuccinimido; acyloxysuccinimido; glutarimido; phenylcarbamoyloxy;

phthalimido; 4-carboxyphthalimido; phthalimidino; 2-pyrrolidono; cyclohexyl; phenyl; phenyl substituted with alkyl, alkoxy, halogen, hydroxy alkanoylamino, carboxy, cyano, or alkoxycarbonyl; alkylsulfonyl; vinylsulfonyl; acrylamido; sulfamyl; benzoylsulfonicimido; alkylsulfonamido; phenylsulfonamido; alkoxycarbonylamino; alkylcarbamoyloxy; groups of the formula

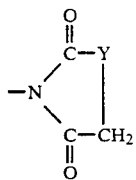

wherein Y is —NH—,

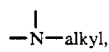

—O—, —S—, or —CH$_2$O; —S—R$_6$; SO$_2$CH$_2$CH$_2$SR$_6$; wherein R$_6$ is alkyl, phenyl, phenyl substituted with halogen, alkyl, alkoxy, alkanoylamino, cyano, or alkoxycarbonyl; pyridyl; pyrimidinyl; benzoxazolyl; benzimidazolyl; benzothiazolyl; radicals of the formula

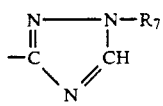

—OXR$_8$; —NHXR$_8$; —X—R$_8$; —CONR$_7$R$_7$; and —SO$_2$NR$_7$R$_7$; wherein R$_7$ is selected from H, aryl, alkyl, and alkyl substituted with halogen, —OH, phenoxy, aryl, —CN, cycloalkyl, alkylsulfonyl, alkylthio, alkanoyloxy, or alkoxy; X is —CO—, —COO—, or —SO$_2$—; R$_8$ is selected from alkyl and alkyl substituted with halogen, hydroxy, phenoxy, aryl, cyano, cycloalkyl, alkylsulfonyl, alkylthio, alkanoyloxy, and alkoxy; and when X is —CO—, R$_8$ also can be hydrogen, amino, alkenyl, alkylamino, dialkylamino, arylamino, aryl, or furyl; alkoxy; alkoxy substituted with hydroxy, cyano, alkanoyloxy, or alkoxy; phenoxy; phenoxy substituted with one or more of alkyl, carboxy, alkoxy, carbalkoxy, or halogen; R$_1$ can also be —R$_2$-Z—B—CH=C(P)Q wherein Z is O or S, and B is arylene;

R$_2$ is alkylene; alkylene substituted with alkoxy, aryl, aryloxy, halogen, hydroxy, acyloxy, cyano, and —Z—B—CH=C(P)Q; arylene, aralkylene, alkylene-O-alkylene; alkylene-O-arylene-O-alkylene; alkylene-arylene-alkylene; alkylene-C$_6$H$_{10}$-alkylene; alkylene-S-alkylene; alkylene-SO$_2$-alkylene;

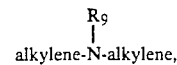

wherein R$_9$ is alkyl, aryl, alkanoyl, alkylsulfonyl, aroyl, or arylsulfonyl;

R$_3$, R$_4$, and R$_5$ are each selected from hydrogen and alkyl;

P and Q and P$^1$ and Q$^1$ are independently selected from cyano, carbalkoxy, carbaryloxy, carbaralkyloxy, carbalkenyloxy, carbamyl, carboxy, acyl, aroyl, N-alkylcarbamyl, N-alkyl-N-arylcarbamyl, N,N-dialkylcarbamyl, N-arylcarbamyl, N-cyclohexylcarbamyl, aryl, 2-benzoxazolyl, 2-benzothiazolyl, 2-benzimidazolyl, 2 or 3-thienyl, 1,3,4-thiadiazol-2-yl, 1,3,4-oxadiazol-2-yl, SO$_2$ alkyl, SO$_2$ aryl, pyridyl, pyrolyl, quinolyl, pyrimidyl and

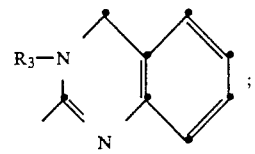

wherein:

in the above definitions, each alkyl, alkoxy, aryl, or cycloalkyl moiety or portion of a group or radical may be substituted where appropriate with hydroxyl, acyloxy, alkyl, cyano, alkoxycarbonyl, halogen, alkoxy, aryl, aryloxy, or cycloalkyl;

and each methine compound, preferably at least one of A, P, Q, P$^1$ or Q$^1$ thereof, bears a group capable of reacting under polymerization conditions, to incorporate the multichromophoric compound into the polymer, including the following: carboxy, carbalkoxy, carbaryloxy, N-alkylcarbamyloxy, acyloxy, chlorocarbonyl, carbamyloxy, N-alkylcarbamyloxy, amino, alkylamino, hydroxyl, N-phenylcarbamyloxy, cyclohexanoyloxy, and carbocyclohexyloxy, wherein the alkyl and/or aryl groups may contain common substituents such as hydroxyl, cyano, acyloxy, carbalkoxy, phenyl, and halogen which do not interfere with the condensation reaction.

In all of the above definitions the alkyl or alkylene moieties or portions of the various groups contain 1–8 carbon atoms, straight or branched chain.

The methine compounds of this invention are preferably prepared by the following synthetic route wherein each B in the formulae is:

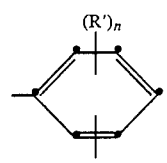

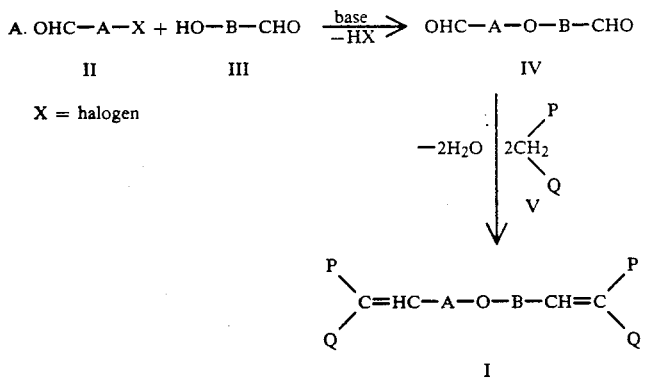

whereby aldehydes II containing reactive displaceable halogens (X) are reacted with p-hydroxybenzaldehydes III under basic conditions to produce bis-aldehydes IV, which are further reacted with active methylenes V under Knoevenagel reaction conditions to produce I. Lower alcohols such as methanol, ethanol, and isopropanol are convenient solvents for condensing intermediates IV with active methylenes V. Bases such as piperidine, piperidine acetate, sodium acetate, and pyridine are effective catalysts in promoting the condensation reaction. Sometimes with the active methylenes of lesser reactivity, completion of reaction may need to be achieved by carrying out the reaction in solvents such as refluxing benzene or toluene whereby the water thus formed can be azeotropically removed as it is formed.

It is also possible to form the compounds of the invention by reacting yellow methine compounds VI and UV absorbing compounds VII, with VI and VII having been prepared

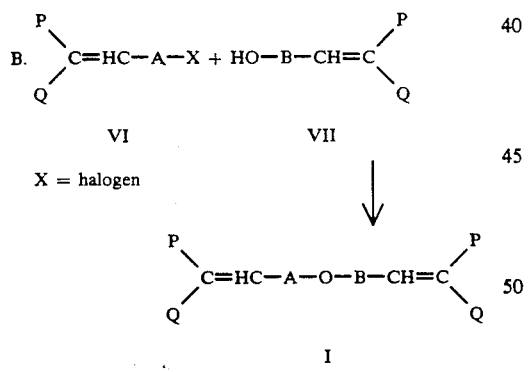

by condensing the corresponding aldehydes with active methylenes V.

Aldehydes II are conveniently prepared by the Vilsmeier-Haack reaction on compounds VIII as follows:

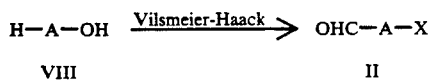

For example, H—A—OH when treated with POCl$_3$ and N,N-dimethylformamide produces OHC—A—Cl.

Another synthetic route is to react compounds IX with III to produce X, which can be converted into I by two different routes.

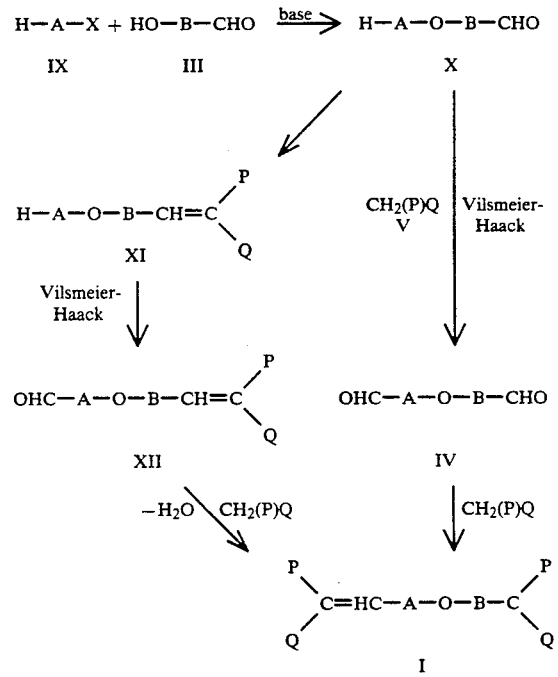

Compounds X undergo the Vilsmeier-Haack formylation reaction to produce bis-aldehydes IV, which can be reacted as shown above with two equivalents of active methylenes V to produce I. Also, X can be reacted with active methylenes V to produce XI, which undergo formylation by Vilsmeier-Haack reaction to produce XII, which yield I when reacted with active methylene V.

The nonextractabilities of the present bis-methine moieties are determined as follows:

EXTRACTION PROCEDURE

All extractions are done in glass containers with distilled solvents under the time and temperature conditions described below. The sample form is $\frac{1}{2}$ inch $\times 2\frac{1}{2}$ inch segments cut from the cylindrical side wall portion of 2-liter bottles. All samples are washed with cold solvent to remove surface contaminants and are exposed using 200 mL solvent/100 in.$^2$ surface area (2 mL/in.$^2$).

Solvent blanks are run under the same extraction conditions without polymer. In most cases samples were extracted, spiked, with a known amount of additive as a control, and analyzed in duplicates.

EXTRACTION CONDITIONS

1. Water. The samples at room temperature are added to solvent and heated at 250° F. for two hours. Half of the samples are then analyzed and the remainder are placed in a 120° F. oven for 30 days and then analyzed.

2. 50% Ethanol/Water. The samples at room temperature are added to the solvent at room temperature, placed in an oven at 120° F. and analyzed after 24 hours and 30 days.

3. Heptane. The samples at room temperature are added to solvent at room temperature and heated at 150° F. for two hours. Part of the samples are cooled to room temperature and analyzed spectrophotometrically and the remainder are allowed to age at 120° F. for 30 days before analysis.

4. Any suitable analytical technique and apparatus may be employed to determine the amount of bis-methine moiety extracted from the polymer.

The extractability of the present bis-methine moieties from the present polymers was found to be essentially nonexistent.

The presently preferred linear polymers employed in the practice of the present invention are thermoplastic molding or fiber grade materials having an I.V. of from about 0.4 to about 1.2, and preferably are polyesters wherein the acid moiety is comprised of at least about 50 mol % terephthalic acid residue, and the glycol moiety at least about 50 mol % ethylene glycol or 1,4-cyclohexanedimethanol residue, and containing a total of from about 1.0 to about 50,000 ppm of one or a mixture of the bis-methine and/or tris-methine moieties described above. The term "acid" as used herein with respect to both the linear and unsaturated polyesters includes their various reactive derivatives such as dimethylterephthalate, anhydrides and the like. A highly preferred polyester within this preferred group is comprised of from about 75 to 100 mol % terephthalic acid residue and from about 75 to 100 mol % ethylene glycol residue.

In accordance with the present invention, the bis-methine or tris-methine moieties derived from the invention compounds described above impart to the polymers the property of ultraviolet and visible light absorption generally significantly within the range of from about 340 nm to about 500 nm. The moieties preferably have molecular weights of from about 280 to about 1,000 although lower or higher molecular weights are also operable and are derived from reactants (monomers) having one or more groups which condense during condensation or polycondensation to enter the moiety into the polymer chain. These groups include hydroxyl, carboxyl, carboxylic ester, acid halide and the like. As aforesaid, these moieties are thermally stable at polymer processing conditions, which includes polycondensation temperatures of up to about 300° C. which are used, for example, in the preparation of polyesters such as poly(ethylene terephthalate) and copolymers of terephthalic acid, ethylene glycol, and 1,4-cyclohexanedimethanol.

Polyesters useful in this invention include broadly linear, thermoplastic, crystalline, or amorphous materials, produced by conventional techniques using one or more diols and one or more dicarboxylic acids, either blended with, or copolymerized with the bis-methine and/or tris-methine moieties. Preferably employed in the practice of the present invention is molding or fiber-grade condensation polymer having copolymerized therein a total of from about 1.0 to about 100,000 ppm, of the reactant residue moieties of one or a mixture of the above-described bis- and tris-methine moieties.

Also useful are the unsaturated, curable polyesters which are the polyesterification products of one or more dihydric alcohols and one or more unsaturated dicarboxylic acids or their anhydrides, and the term "polyester resin" is used herein to define the unsaturated polyester dissolved in or admixed with an ethylinically unsaturated monomer. Typical of the unsaturated polyesters is the polyesterification product of (a) 1,4-cyclohexanedimethanol and/or 2,2-dimethyl-1,3-propanediol and optionally an additional dihydric alcohol, such as ethylene glycol, and (b) maleic acid or fumaric acid and an unsaturated hydrogenated aromatic dicarboxylic acid, which when crosslinked with an ethylenically-unsaturated monomer, e.g., styrene, produces a cured polyester resin which has, for example, high thermal resistance, high heat distortion values, excellent electrical and mechanical properties, and excellent resistance to chemicals.

The unsaturated polyester resins may be prepared in the presence of gelation inhibitors such as hydroquinone or the like, which are well known in the art of polyesterification. The esterification may be carried out for example under an inert blanket of gas such as nitrogen in a temperature range of 118°–220° C. for a period of about 6–20 hours until an acid number below 100 and preferably below 50 is obtained, based on milliequivalents of KOH necessary to neutralize 1 gram of the unsaturated polyester. The resulting polyester may be subsequently copolymerized, cross-linked, or cured with "curing amounts" of any of the well-known ethylenically unsaturated monomers used as solvents for the polyester. Examples of such monomers include styrene, alpha-methyl styrene, vinyl toluene, divinyl benzene, chlorostyrene, and the like as well as mixtures thereof. Typically, the mole ratio of such unsaturated monomer to the unsaturated moiety (e.g., maleic acid residue) in the polyester is from about 0.5 to about 3.0, although the "curing amounts" of such monomer can be varied from these ratios.

It is preferred that the unsaturated polyester be prepared from one or more dihydric alcohols, fumaric or maleic acid or mixtures thereof, and up to about 60 mole percent of total acid component of o-phthalic, isophthalic or terephthalic acids or mixtures thereof. Preferred for the dihydric alcohol component is one or a mixture of propylene glycol, neopentyl glycol, 2,2,4-trimethyl-1,3-pentanediol, ethylene glycol, or diethylene glycol. A specific preferred unsaturated polyester is prepared from about 75 to 100 mol % propylene glycol, and as the acid component, from about 75 to 100 mol % phthalic and maleic acids in a mole ratio of from about ½ to about 2/1. Typical of these unsaturated polyesters are those disclosed, for example, in U.S. Pat. No. 4,359,570 incorporated herein by reference.

The diol components of the linear polyester are selected, for example, from ethylene glycol, 1,4-cyclohexanedimethanol, 1,2-propanediol, 1,3-propanediol, 1,4-butanediol, 2,2-dimethyl-1,3-propanediol, 1,6-hexanediol, 1,2-cyclohexanediol, 1,4-cyclohexanediol, 1,2-cyclohexanedimethanol, 1,3-cyclohexanedimethanol, X, 8-bis(hydroxymethyl)-tricyclo-[5.2.1.0]-decane wherein X represents 3, 4, or 5; and diols containing one or more oxygen atoms in the chain, e.g., diethylene glycol, triethylene glycol, dipropylene glycol, tripropylene glycol and the like. In general, these diols contain 2 to 18, preferably 2 to 12 carbon atoms. Cycloaliphatic diols can be employed in their cis or trans configuration or as mixtures of both forms.

The acid components (aliphatic, alicyclic, or aromatic dicarboxylic acids) of the linear polyester are selected, for example, from terephthalic acid, isophthalic acid, 1,4-cyclohexanedicarboxylic acid, 1,3-cyclohexanedicarboxylic acid, succinic acid, glutaric acid, adipic acid, sebacic acid, 1,12-dodecanedioic acid, 2,6-naphthalene-dicarboxylic acid and the like. In the polymer preparation, it is often preferable to use a functional acid derivative thereof such as the dimethyl, diethyl, or dipropyl ester of the dicarboxylic acid. The anhydrides of these acids also can be employed where practical.

The preferred linear copolyesters are especially useful for making blow molded bottles or containers for beverages, and for molded food packages and the like. In this regard, certain of these copolyesters are color, I.V., and heat distortion or "hot fill" stable at temperatures of up to about 100° C., when properly heat set and molded articles therefrom exhibit good thin wall rigidity, excellent clarity and good barrier properties with respect to water and atmospheric gases, particularly carbon dioxide and oxygen.

In regard to products having the "hot fill" stability, the most preferred linear polyesters therefor comprise poly(ethylene terephthalate) and this polymer modified with up to about 5 mole % of 1,4-cyclohexanedimethanol, wherein the polymers have been sufficiently heat set and oriented by methods well known in the art to give a desired degree of crystallinity. By definition, a polymer is "hot fill" stable at a prescribed temperature when less than 2% change in volume of a container manufactured therefrom occurs upon filling the same with a liquid at that temperature. For the particular application of blow-molded beverage bottles, the most preferred polyesters have an I.V. of 0.65 to 0.85, and a Tg of >70° C., and film sections cut from the bottle have a Water Vapor Transmission Rate of 1.5 to 2.5 g. mils/100 in.$^2$-24 hrs., a $CO_2$ Permeability of 20-30 cc. mils/100 in.$^2$-24 hrs.-atm., and an $O_2$ Permeability of 4-8 cc. mils/100 in.$^2$-24 hrs.-atm. The Tg is determined by Differential Scanning Calorimetry at a scan rate of 20 Centigrade Degrees/min., the $O_2$ Permeability by the standard operating procedure of a MOCON OXTRAN 100 instrument of Modern Controls, Inc., of Elk River, Minnesota, and the $CO_2$ Permeability by the standard operating procedure of a MOCON PERMATRAN C II, also of Modern Controls.

Typical polycarbonates useful herein are disclosed in Kirk-Othmer Encyclopedia of Chemical Technology, third edition, Volume 18, pages 479-494, incorporated herein by reference.

EXAMPLES

The examples below and following tables further illustrate the practice and scope of the invention.

The inherent viscosities (I.V.) of each of the copolyesters herein were determined according to ASTM D2857-70 procedure in a Wagner Viscometer of Lab Glass Inc. of Vineland, N.J. having a ½ mL capillary bulb, using a polymer concentration of 0.5% by weight in 60/40 by weight, phenol/tetrachloroethane solvent. The procedure comprises heating the polymer/solvent system at 120° C. for 15 minutes to enhance dissolution of the polymer, cooling the solution to 25° C. and measuring the time of flow at 25° C. The I.V. is calculated from the equation $$\{\eta\}_{0.50\%}^{25°\,C.} = \frac{\ln \frac{t_s}{t_o}}{C}$$

where:
$\{\eta\}$ = Inherent viscosity at 25° C. at a polymer concentration of 0.5 g./100 mL of solvent;
ln = Natural logarithm;
$t_s$ = Sample flow time;
$t_o$ = Solvent-blank flow time; and
C = Concentration of polymer in grams per 100 mL of Solvent = 0.5.

EXAMPLE 1

Preparation of 4-[[2-(4-Formylphenoxy)ethyl]ethylamino]benzaldehyde

A mixture of 4-[[2-Chloroethyl]ethylamino]benzaldehyde 10.6 g (0.05 m), p-hydroxybenzaldehyde (6.1 g, 0.05 m), 50% NaOH (4.4 g), water (50 mL), and 2-(2-ethoxyethoxy)ethanol was heated at reflux for 6 hours and then allowed to cool. A semi-solid product was obtained which was washed with water by decantation and recrystallized from methanol. After being collected by filtration, washed with methanol, and dried in air the product weighed 6.5 g and the structure was confirmed by mass spectral analysis to be as follows:

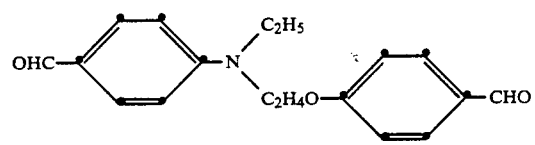

EXAMPLE 2

Preparation of Methyl 2-cyano-3-[4-[2-[[4-(2-cyano-3-methoxy-3-oxo-1-propenyl)phenyl]ethylamino]ethoxy]phenyl]propenoate A mixture of 4-[[2-(4-formylphenoxy)ethyl]ethylamino]benzaldehyde (1.49 g, 0.005 m) from Example 1, methyl cyanoacetate (1.48 g, 0.015 m), methanol (20 mL), and piperidine (6 drops) was heated at reflux for 2 hours. The yellow product, which formed during this heating time, was collected by filtering the hot reaction mixture, washed with methanol, and dried in air. It weighed 0.75 g, had a bright orange fluorescence under long wavelength UV light, and has the following structure as indicated by mass spectral analysis:

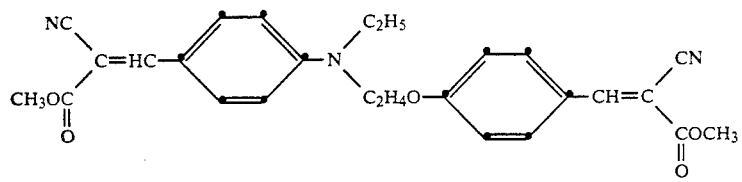

Absorption Maxima - 340 nm, 419 nm (acetone)

When dissolved in acetone, the compound absorbs visible light with a maximum absorption (λmax) at 419 nm and UV light at a maximum of about 340 nm.

EXAMPLE 3

Preparation of Methyl 2-cyano-3-[4-[2-[[4-(2-cyano-3-methoxy-3-oxo-1-propenyl)-3-methylphenyl]ethylamino]ethoxy]-3-methoxyphenyl]propenoate Vanillin (7.6 g, 0.05 m) was dissolved in water (50 mL) containing 4.4 g of 50% NaOH by stirring. 4-[(2-chloroethyl)ethylamino]o-tolualdehyde (11.3 g, 0.05 m) was added and the mixture was heated at reflux for 6 hours. Additional water (100 mL) was added and the bis-aldehyde intermediate was washed by decantation. The oily product was washed once more with water by decantation and then dissolved in hot methanol (75 mL). Methyl cyanoacetate (9.9 g, 0.1 m) and piperidine (1 mL) were added and the reaction mixture was heated at reflux for 1.5 hours. During the heating period, the yellow product crystallized and was collected by filtering hot, washed with methanol, and dried in air. The yield of product was 10.0 g which has the following structure by mass spectral analysis:

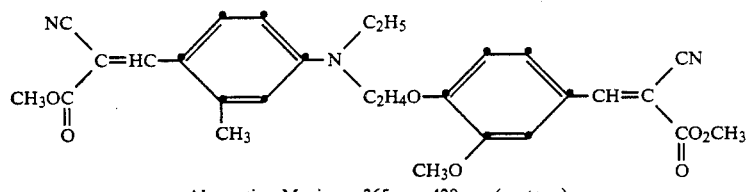

Absorption Maxima - 365 nm, 429 nm (acetone)

When dissolved in acetone, the compound absorbs visible light with a maximum absorption (λmax) at 429 nm and UV light at a maximum of about 365 nm.

EXAMPLE 4

Preparation of 2-Cyano-3-[4-[2-[[2-cyano-3-methoxy-3-oxo-1-propenyl)phenyl]ethylamino]ethoxy]-3-methoxyphenyl]propenoate A mixture of 4-[(2-chloroethyl)ethylamino]benzaldehyde (10.5 g, 0.05 m), vanillin (9.1 g, 0.06 m), water (35 mL), 2-ethoxyethanol (10 mL), and 50% NaOH (4.8 g) was heated at reflux for 3 hours.

The mixture was allowed to cool and the aqueous layer removed. Methanol (50 mL) and methyl cyanoacetate (11.0 g, 0.11 m), piperidine (10 drops) and acetic acid (5 drops) were added to the organic layer. The reaction mixture was heated at reflux for 1 hour. During the heating period the yellow product crystallized and was collected by hot filtration, washed with methanol, and dried in air (yield 9.5 g). The product has a bright orange fluorescence under long wavelength UV light and has the following structure as confirmed by mass spectrum analysis:

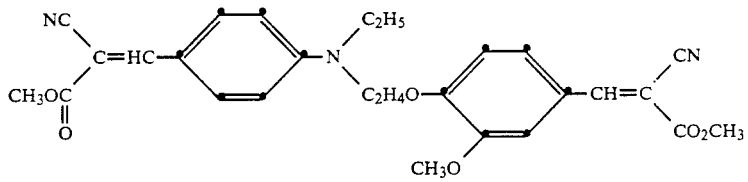

Absorption Maxima - 365 nm, 422 nm (acetone)

When dissolved in acetone, the product absorbs UV light at a maximum (λmax) at 365 nm and has an absorption maximum in the visible absorption spectrum at 422 mn.

EXAMPLE 5

Dimethyl 2,2'-dicyano-3,3'-[[[4-(2-cyano-3-methoxy-3-oxo-1-propenyl)phenyl]imino] bis [2,1-ethanediyloxy)(3-methoxy-4,1-phenylene)]]bis-propenoate A mixture of 4-[(di-2-chloroethyl)amino]benzaldehyde (2.46 g, 0.01 m), vanillin (3.04 g, 0.02 m), water (25 mL), 2-ethoxyethanol (10 mL), and 50% NaOH (1.8 g) was heated at 100° C.–105° C. for 8 hours. Additional quantities of vanillin (1.52 g, 0.01 m) and 50% NaOH (0.8 g) were added and heating continued for an additional 4 hours at ~105° C. The reaction mixture was allowed to cool and the aqueous layer removed by decantation, followed by two additional water washes by decantation. To the organic layer were added methyl cyanoacetate (3.0 g, 0.03 m), N,N-dimethylformamide (20 mL), methanol (75 mL), and piperidine (6 drops). The reaction mixture was heated at reflux for 1.5 hours and then allowed to cool. The product was collected by filtration, washed with methanol, and dried in air. Mass spectral analysis showed a mixture of products, mostly the tri-chromophoric compound A, with a smaller amount of the di-chromophoric compound B.

container showed a strong, broad absorption peak from 360 to 440 nm. Analyses of the condensate collected during the polycondensation after adding the multi-chromophoric compound using a Perkin Elmer Lambda 4B Spectrophotometer showed less than 1%

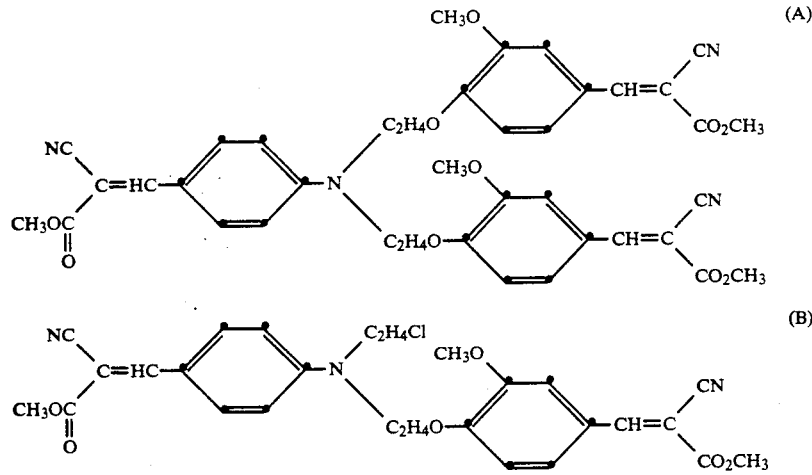

(A)

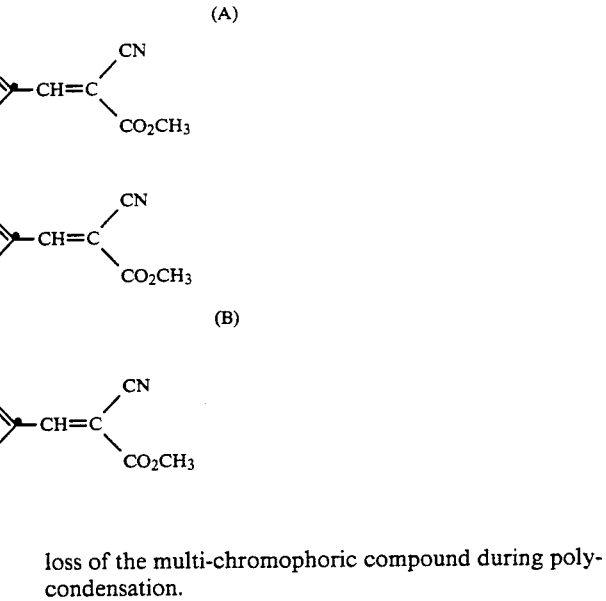

(B)

When the product was dissolved in acetone, absorption maxima were observed at 370 nm in the UV absorption spectrum and at 412 nm in the visible absorption spectrum.

loss of the multi-chromophoric compound during polycondensation.

EXAMPLE 6

Preparation of Poly(ethylene terephthalate) Copolymerized with Dimethyl 2,2'-dicyano-3,3'-[[[4-(2-cyano-3-methoxy-3-oxo-1-propenyl)phenyl]imino] bis [(2,1-ethanediyloxy)(3-methoxy-4,1-phenylene]]bis propenoate The following compounds were placed in 500-mL, 3-necked, round-bottom flask:
97 g (0.5 mol) dimethyl terephthalate
62 g (1.0 mol) ethylene glycol
0.0345 g $Sb_2O_3$
0.19 mL of a n-butanol solution of acetyltriisopropyl titanate which contained 0.0057 g Ti.

The reaction flask was equipped with a nitrogen inlet, stirrer, vacuum outlet, and condensing flask. The flask and contents were heated at 200° C. in a Belmont metal bath for 60 minutes and at 210° C. for 75 minutes with a nitrogen sweep over the reaction mixture. Then 0.48 mL of an ethylene glycol slurry of Zonyl A which contains 0.0038 g phosphorous was added. The temperature of the bath was increased to 230° C. At 230° C., 0.0384 g dimethyl 2,2'-dicyano-3,3'-[[[4-(2 cyano-3-methoxy-3-oxo-1-propenyl)phenyl]imino] bis [(2,1-ethanediyloxy) (3-methoxy-4,1-phenylene)]]bis propenoate were added to the flask.

Five minutes after this addition, the temperature of the bath was increased to 285° C. When the bath temperature reached 270° C., vacuum was applied directly to the flask. The flask and contents were heated by 270°–285° C. under a pressure of 0.1 mm Hg for 29 minutes. The flask was removed from the metal bath and was allowed to cool in nitrogen atmosphere while the polymer crystallized. The resulting polymer had an inherent viscosity of 0.62 measured in a 60/40 ratio by weight of phenol/tetrachloroethane at a concentration of 0.5 g per 100 mL. An amorphous 13 mil thick film molded from this polymer to simulate the sidewall of a

EXAMPLE 7

Preparation of Green Poly(ethylene terephthalate) with Reduced Light Transmittance by Copolymerizing with a Multi-Chromophoric Compound The following compounds were placed in 500-mL, three-necked, round-bottom flask:
97 g (0.5 mol) dimethyl terephthalate
62 g (1.0 mol) ethylene glycol
0.29 mL of a n-butanol solution of acetyl-triisopropyl titanate which contained a 0.0087 g Ti.

The reaction flask was equipped with a nitrogen inlet, stirrer, vacuum outlet, and condensing flask. The flask and contents were heated at 200° C. in a Belmont metal bath for 60 minutes and at 210° C. for 75 minutes with a nitrogen sweep over the reaction mixture. The temperature of the bath was increased to 230° C. At 230° C., 0.0072 g of copper phthalocyanine blue and 0.0384 g dimethyl 2,2'-dicyano-3,3'-[[[4-(2 cyano-3-methoxy-3-oxo-1-propenyl)phenyl]imino] bis [(2,1-ethanediyloxy)(3-methoxy-4,1-phenylene)]]bis propenoate were added to the flask. Five minutes after this addition, a vacuum with a slow stream of nitrogen bleeding in the system was applied over a five-minute period until the pressure was reduced to 200 mm Hg. The flask and contents were heated at 230° C. under a pressure of 200 mm Hg for 25 minutes. The metal bath temperature was increased to 270° C. At 270° C. the pressure was reduced slowly to 100 mm Hg. The flask and contents were heated at 270° C. under a pressure of 100 mm Hg for 30 minutes. The metal bath temperature was increased to 285° C. and the pressure was reduced slowly to 4.5 mm Hg. The flask and contents were heated at 285° C. under a pressure of 4.5 mm Hg for 25 minutes. Then the pressure was reduced to 0.25 mm Hg and polycondensation was continued at 285° C. for 16 minutes. The flask was removed from the metal bath and allowed to cool in nitrogen atmosphere while the polymer crystallized. The resulting polymer was green colored and had an inherent viscosity of 0.63 measured in a 60/40 ratio by weight of phenol/tetrachloroethane at a concentration of 0.5 g per 100 mL. An amorphous 13 mil thick film made from this polymer to simulate the sidewall of a container transmitted less than 10% light at all wavelengths less than 426 nm while a 13 mil film prepared from a poly(ethylene terephthalate) control transmitted greater than 10% light at all wavelengths above 320 nm.

EXAMPLE 8

Preparation of Polyester Unsaturated Resin of Neopentyl Glycol, Isophtahlic Acid, and Maleic Anhydride Copolymerized with Multi-Chromophoric Methine Compound and Crosslinked with Styrene A three-liter reaction flask was fitted with a stirrer, thermometer, nitrogen inlet tube, and a heated Vigreux column. The top of the Vigreux column was also fitted with a Dean-Stark trap and a cold water condenser. The flask was charged with 763 g of neopentyl glycol (7.34 moles), 598 g of isophthalic acid (3.6 moles) and 0.608 g (400 PPM) of the following compound:

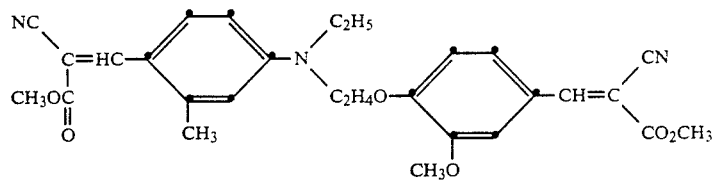

The monomers were reacted at 200° C. until the theoretical amount of distillate was collected (approximately 4 hours at 200° C. to collect 118 mL distillate). The reaction mixture was cooled to 150° C. and 353 g of maleic anhydride (3.6 moles) were added. The reaction was continued at 200° C. for 7 hours until an acid number of 20 was obtained. The resulting bright yellow unsaturated polyester was cooled to a temperature of 140° C. and diluted to 45% with styrene monomer. Benzoyl peroxide was added at 1 weight % to a portion of this polyester-styrene mixture and a 30 mil thick casting was prepared and cured at 100° C. A UV-visible spectrum of the resulting bright yellow thermoset sheet showed a strong broad absorption peak with a maximum at 430 nm.

TABLE 1

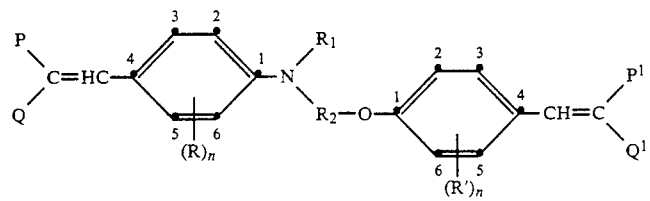

| Example No. | P | Q | (R)$_n$ | R$_1$ |
|---|---|---|---|---|
| 9 | CN | COOCH$_3$ | H | C$_2$H$_5$ |
| 10 | CN | COOC$_2$H$_5$ | 3-CH$_3$ | C$_4$H$_{9-n}$ |
| 11 | CN | COOC$_4$H$_{9-n}$ | 3-Cl | CH(CH$_3$)$_2$ |
| 12 | CN | COOC$_2$H$_4$OH | 2-OCH$_3$ | C$_2$H$_5$ |
| 13 | CN | COOC$_2$H$_4$OH | 2,5-di-OCH$_3$ | CH$_2$CH$_2$Cl |
| 14 | CN | COOCH$_3$ | H | C$_2$H$_5$ |
| 15 | CN | COOCH$_3$ | H | C$_6$H$_5$ |
| 16 | CN | COOCH$_3$ | H | C$_6$H$_4$-p-COOCH$_3$ |
| 17 | CN | COOH | 2,5-di-CH$_3$ | C$_6$H$_{11}$ |
| 18 | COOCH$_3$ | COOCH$_3$ | H | CH$_3$ |
| 19 | CN | CN | H | C$_2$H$_5$ |
| 20 | CN | SO$_2$CH$_3$ | 3-CH$_3$ | C$_2$H$_5$ |
| 21 | CN | SO$_2$C$_6$H$_5$ | 3-Br | 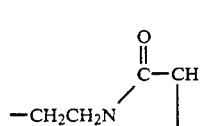 |
| 22 | CN | 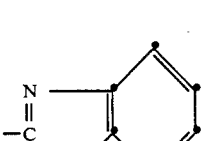 | H | C$_2$H$_5$ |

TABLE 1-continued

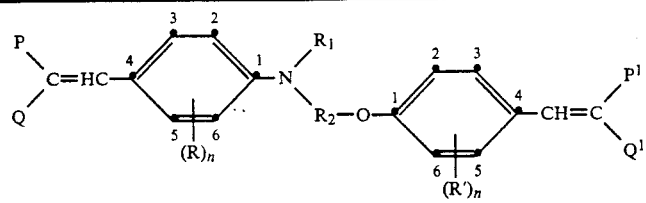

| | P,Q | R₁ | (R)ₙ | R₂ |
|---|---|---|---|---|
| 23 | CO₂C₂H₅ | (benzoxazole) | H | C₂H₅ |
| 24 | CN | (benzoyl) | H | C₂H₅ |
| 25 | CN | CONHC₂H₄OH | H | CH₂CH₂OC₂H₅ |
| 26 | CN | CONH₂ | H | CH₂C₆H₅ |
| 27 | CN | (4-methoxyphenyl) | 3-CH₃ | CH₂C₆H₁₁ |
| 28 | CN | (benzothiazole) | 2-OCH₃, 5-CH₃ | CH₂CH₂OC₆H₅ |
| 29 | CN | (oxadiazole) | 3-CH₂OH | CH₂CH₂OCCH₃ (O=) |
| 30 | CN | (thiophene-CO) | 3-CH₂OCCH₃ | CH₂CH₂CH₂OCC₆H₅ (O=) |
| 31 | CN | (N-methylpyrrole) | 3-CH₃ | CH₂CH₂N(phthalimide) |
| 32 | CN | (phenyl) | 3-F | CH₂CH₂N(hydantoin) |
| 33 | CN | (quinazolinone) | 3-CH₃ | C₆H₅ |

TABLE 1-continued

Structure header: P/Q-C=CH-[phenyl(4,3,2,1,6,5) with (R)ₙ and R₁ on N]-N(R₁)-R₂-O-[phenyl(1,2,3,4,6,5) with (R')ₙ]-CH=C-P¹/Q¹

| # | P | R₂ | (R)ₙ | R₁ |
|---|---|---|---|---|
| 34 | CN | 1,3,4-thiadiazol-2,5-diyl (N=N, S) | 3-C₆H₅ | -CH₂-(thiophene-2,5-diyl)-CH₂OH |
| 35 | CN | COC(CH₃)₂ | 3-SC₆H₅ | CH₂CH₂C₆H₅ |
| 36 | CH₃SO₂ | CO₂C₂H₅ | 3-OCH₃ | CH₂CH=CH₂ |
| 37 | CN | CO₂C₂H₅ | H | CH₂CH₂O-C₆H₄-CH=C(CN)₂ |
| 38 | CN | CN | H | CH₂CH₂O-C₆H₄-CH=C(CN)(CO₂CH₃) |
| 39 | CO₂C₂H₅ | 2-(2-imino)benzimidazolyl | H | C₂H₄CN |
| 40 | CN | CONH-C₆H₅ | H | CH₂CH₂NHSO₂CH₃ |
| 41 | CN | CONH-C₆H₄-CH₂OH | H | -CH₂CH₂S-C(=N-benzothiazolyl)-S- (2-benzothiazolyl-SCH₂CH₂-) |
| 42 | CN | CONH-(thiophene) | H | -CH₂CH₂-S-(1,2,4-triazol-3-yl) |
| 43 | CN | CO₂CH₂C₆H₅ | H | -CH₂CH₂SO₂NHC₂H₅ |
| 44 | CN | CO₂CH₂-(thiophene) | H | -CH₂CH₂OC(O)NHC₆H₅ |
| 45 | CN | CO₂-(thiophene) | H | -CH₂CH₂OC(O)OC₂H₅ |

TABLE 1-continued

| No. | P | R₂ | (R)ₙ | R₁ |
|---|---|---|---|---|
| 46 | CN | [4-methylphenyl-CO₂-CH₂ group] | H | —CH₂CH₂CONH₂ |
| 47 | CN | [furan-CO₂CH₂ group] | H | —CH₂CH₂OCH₂CH₃ |
| 48 | CN | [tetrahydrofuran-CO₂CH₂ group] | H | —CH₂CH₂SCH₃ |
| 49 | CN | CO₂C₂H₅ | 3-OCH₃ | —CH₂CH₂O—[3-CH₃O-phenyl]—CH(CN)(CO₂C₂H₅) |
| 50 | CN | CO₂(CH₂)₂OCH₃ | 3-OCH₃ | C₂H₅ |
| 51 | CN | CO₂CH(CH₃)₂ | 2,5-di-OCH₃ | C₂H₅ |
| 52 | CN | CO₂CH₃ | 3-O—CH₃ | C₆H₄-p-CH₃ |
| 53 | CN | CO₂CH₃ | 3-OC₂H₄OH | C₂H₅ |

| Example No. | R₂ | (R')ₙ | P¹ | Q¹ |
|---|---|---|---|---|
| 9 | —CH₂CH₂OCH₂CH₂— | H | CN | COOCH₃ |
| 10 | —CH₂CH₂CH₂— | H | CN | COOC₂H₅ |
| 11 | —CH₂CH₂SCH₂CH₂— | 2-OCH₃ | CN | COOC₄H₉₋ₙ |
| 12 | —CH₂CH(OH)CH₂— | 3-CH₃ | CN | COOC₂H₄OH |
| 13 | —CH₂—[phenyl]—CH₂— | H | CN | COOC₂H₄OH |
| 14 | —CH₂CH—CH₂— with O—[phenyl]—CH=C(CN)(COOCH₃) branch | H | CN | COOCH₃ |
| 15 | —CH₂CH₂— | H | CN | COOCH₃ |
| 16 | —CH₂CH(OCH₃)CH₂— | H | CN | COOCH₃ |
| 17 | —CH₂CH₂CH₂CH₂— | H | CN | COOH |
| 18 | —CH₂CH₂— | H | COOCH₃ | COOCH₃ |
| 19 | —CH₂CH₂— | H | CN | CN |
| 20 | —CH₂CH₂SO₂CH₂CH₂— | H | CN | COOCH₃ |
| 21 | —CH₂CH₂O—[phenyl]—OCH₂CH₂— | H | COOCH₃ | COOCH₃ |

TABLE 1-continued

Structure header:

P\Q C=CH — [phenyl ring with positions 3,2 / 4 / 1 / 5,6 (R)ₙ] — N(R₁)(R₂) — O — [phenyl ring with positions 2,3 / 1 / 4 / 6,5 (R')ₙ] — CH=C P¹/Q¹

| No. | R₁/R₂ linker | (R)ₙ | Q / Q¹ | P¹ (ring) |
|---|---|---|---|---|
| 22 | —CH₂CH₂— | 2-OCH₃ | CN | benzoxazole (N=C–O fused to benzene) |
| 23 | —CH₂CH₂— | 2-OCH₃ | CO₂C₂H₅ | benzoxazole (N=C–O fused to benzene) |
| 24 | —CH₂CH₂N(SO₂CH₃)CH₂CH₂— | 2,6-diCH₃ | CN | C(=O)–phenyl (benzoyl) |
| 25 | —CH₂CH₂— | H | CN | CONHC₂H₄OH |
| 26 | —CH₂CH₂N(CH₃)CH₂CH₂— | H | COOCH₃ | COOCH₃ |
| 27 | —CH₂CH₂N(SO₂C₂H₅)CH₂CH₂— | 2-OCH₃ | CN | phenyl-OCH₃ (4-methoxyphenyl) |
| 28 | —CH₂CH(OH)CH₂— | 3,5-di-CH₃ | CN | CN |
| 29 | —CH₂CH₂CH₂CH₂— | 2-OCH₃ | CN | oxadiazole (N=N, O ring) |
| 30 | —CH₂CH₂— | H | CN | thiophene with CO substituent (CO–[thiophene-S]) |
| 31 | —CH₂CH(OC₄H₉-n)CH₂— | H | CN | N-methylpyrrole |
| 32 | —CH₂CH₂— | H | CN | pyridine |
| 33 | —CH₂CH(OH)CH₂— | H | CN | COOCH₃ |
| 34 | —CH₂CH₂— | H | CN | 1,3,4-thiadiazole (N=C–S–CH=N) |

TABLE 1-continued

| # | R₂ | R | Q | Q¹ |
|---|---|---|---|---|
| 35 | —CH₂CH₂— | H | CN | COC(CH₃)₃ |
| 36 | —CH₂CH₂— | H | CH₃SO₂ | CO₂C₂H₅ |
| 37 | —CH₂CH₂— | H | CN | CN |
| 38 | —CH₂CH₂— | H | CN | CO₂CH₃ |
| 39 | —CH₂CH₂— | 2-OCH₃ | CO₂C₂H₅ | 2-methylbenzimidazol-2-yl |
| 40 | —CH₂CH₂N(COC₆H₄)—CH₂CH₂— | 2-OCH₃ | CN | —CONH—C₆H₄ |
| 41 | —CH₂CH₂N(C₆H₅)CH₂CH₂— | 2-OCH₃ | CN | —CONH—C₆H₃(CH₂OH) |
| 42 | —CH₂CH₂— | 3-Cl | CN | CO₂CH₃ |
| 43 | —CH₂CH₂— | 2-Cl | CN | CO₂CH₂C₆H₅ |
| 44 | —CH₂CH(OCOCH₃)CH₂— | 2-CH₃ | CN | CO₂CH₂-(thiophene) |
| 45 | —CH₂CH₂— | H | CN | CO₂-(thiophene) |
| 46 | —CH₂CH₂— | H | CN | CO₂-(4-methylphenyl) |
| 47 | —CH₂CH₂— | H | CN | CO₂CH₂-(furan) |
| 48 | —CH₂CH₂— | 2-OCH₂C₆H₅ | CN | CO₂CH₂-(furan) |
| 49 | —CH₂CH₂— | 2-OCH₃ | CN | CO₂C₂H₅ |

TABLE 1-continued
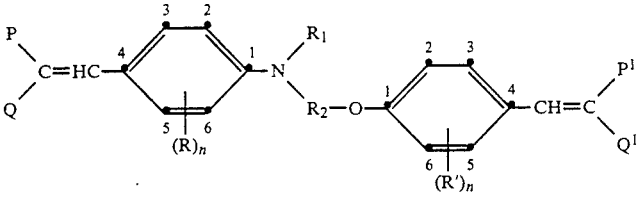
| | | | | |
|---|---|---|---|---|
| 50 | ⬡—CH₂— | 2-OCH₃ | CN | CO₂(CH₂)₂OCH₃ |
| 51 | —CH₂—⬡S—CH₂— | 2-OCH₃ | CN | CO₂CH(CH₃)₂ |
| 52 | —CH₂CH₂— | 2-OCH₃ | CN | CO₂CH₃ |
| 53 | —CH₂CH₂— | 2-OC₄H₉₋ₙ | CN | CO₂CH₃ |

TABLE 2

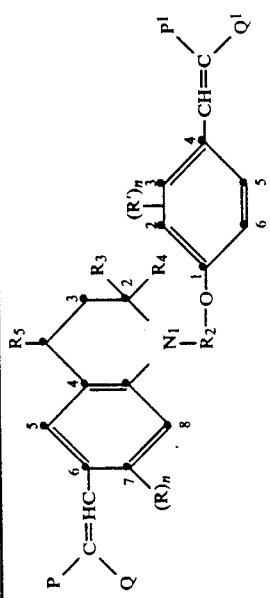

| Example No. | P | Q | (R)$_n$ | R$_3$ | R$_4$ | R$_5$ | R$_2$ | (R')$_n$ | P$^1$ | Q$^1$ |
|---|---|---|---|---|---|---|---|---|---|---|
| 54 | CN | CO$_2$CH$_3$ | H | CH$_3$ | CH$_3$ | CH$_3$ | —CH$_2$CH$_2$— | H | CN | CO$_2$CH$_3$ |
| 55 | CN | CO$_2$CH$_3$ | H | H | H | H | —CH$_2$CH$_2$— | H | CN | CO$_2$CH$_3$ |
| 56 | CN | CO$_2$C$_2$H$_5$ | H | H | CH$_3$ | H | —CH$_2$CH$_2$CH$_2$— | H | CN | CO$_2$C$_2$H$_5$ |
| 57 | CN | CO$_2$C$_4$H$_{9-n}$ | H | H | CH(CH$_3$)$_2$ | H | —CH$_2$CH$_2$OCH$_2$CH$_2$— | H | CN | CO$_2$C$_4$H$_{9-n}$ |
| 58 | CN | CO$_2$H | 7-CH$_3$ | CH$_3$ | CH$_3$ | CH$_3$ | —CH$_2$CH$_2$CH$_2$— | H | CN | CO$_2$H |
| 59 | CN | CO$_2$H | 7-OCH$_3$ | CH$_3$ | CH$_3$ | CH$_3$ | —CH$_2$CH$_2$— | H | CN | CO$_2$H |
| 60 | CN | CO$_2$CH$_3$ | H | CH$_3$ | CH$_3$ | CH$_3$ | —CH$_2$CH$_2$— | 2-OCH$_3$ | CN | CO$_2$CH$_3$ |
| 61 | CN | CO$_2$CH$_3$ | 7-OCH$_3$ | H | CH$_3$ | H | —CH$_2$CHCH$_2$—O— with CH$_3$O substituent and CN/CO$_2$CH$_3$ vinyl | 2-OCH$_3$ | CN | CO$_2$CH$_3$ |
| 62 | CN | CN | H | CH$_3$ | CH$_3$ | CH$_3$ | —CH$_2$CH$_2$— | 2-OCH$_3$ | CN | CO$_2$CH$_3$ |
| 63 | CN | CN | 7-Cl | H | CH$_3$ | H | —CH$_2$CH$_2$— | 2-OCH$_3$ | CO$_2$CH$_3$ | CO$_2$CH$_3$ |
| 64 | CO$_2$CH$_3$ | CO$_2$CH$_3$ | 5-CH$_3$, 8-OCH$_3$ | CH$_3$ | CH$_3$ | CH$_3$ | —CH$_2$CH$_2$— | 2-OCH$_3$ | CO$_2$CH$_3$ | CO$_2$CH$_3$ |
| 65 | CN | CO$_2$C$_2$H$_4$OCH$_3$ | 5,8-di-CH$_3$ | H | CH$_3$ | H | —CH$_2$CH$_2$SCH$_2$CH$_2$— | 3-CH$_3$ | CN | CO$_2$C$_2$H$_4$OCH$_3$ |
| 66 | CN | CO$_2$C$_2$H$_4$OH | 8-OCH$_3$ | CH$_3$ | CH$_3$ | CH$_3$ | —CH$_2$—⌬—CH$_2$— | 2-OC$_2$H$_5$ | CN | CO$_2$C$_2$H$_4$OH |
| 67 | CN | 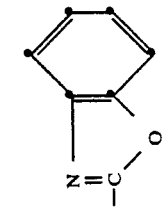 | 7-OCH$_3$ | H | CH$_3$ | H | —CH$_2$—(S-ring)—CH$_2$— | 2-OC$_4$H$_{9-n}$ | CN | 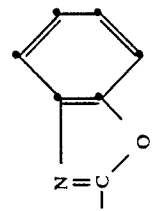 |

TABLE 2-continued
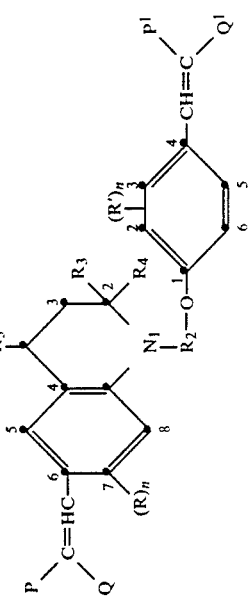
| Example No. | P | Q | (R)n | R3 | R4 | R5 | R2 | (R')n | P1 | Q1 |
|---|---|---|---|---|---|---|---|---|---|---|
| 68 | CO2C2H5 |  | H | CH3 | CH3 | CH3 | —CH2CH2CH2CH2— | 2-OCH2C6H5 | CN | CN |
| 69 | CO2C2H5 | 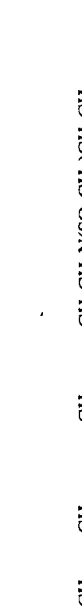 | 7-OCH3 | CH3 | CH3 | CH3 | —CH2CH2SO2CH2CH2— | 3,5-di-CH3 | CO2C2H5 |  |
| 70 | CN |  | 7-Br | CH3 | CH3 | CH3 | —CH2CH2N(SO2CH3)CH2CH2— | 3-CH3 | CN |  |
| 71 | CN |  | 7-CH3 | | | CH3 | —CH2CH2N(C6H5)CH2CH2— | 2-CH3 | CN | |
| 72 | CN | CO2CH3 | 7-CH3 | CH3 | CH3 | CH3 | —CH2CH2— | 2-OCH3 | CN | CN |
| 73 | CN | SO2CH3 | H | H | H | H | —CH2CH2CH2— | 2-OCH3 | CN | CO2CH3 |
| 74 | CN | CONHC2H4OH | 7-CH3 | H | CH3 | H | —CH2CH2— | 2-OCH3 | CN | CONHC2H4OH |

TABLE 2-continued

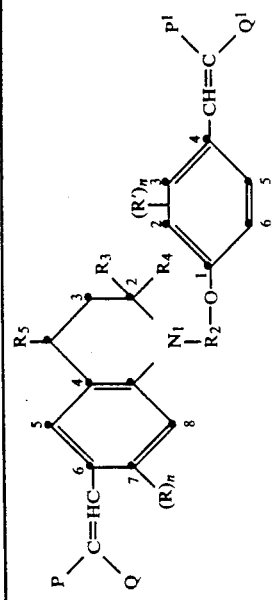

| Example No. | P | Q | (R)ₙ | R₃ | R₄ | R₅ | R₂ | (R')ₙ | P¹ | Q¹ |
|---|---|---|---|---|---|---|---|---|---|---|
| 75 | CN | CONHC₆H₅ | H | CH₃ | CH₃ | CH₃ | —CH₂CH(OH)CH₂— | 2-OCH₃ | CN | CONHC₆H₅ |
| 76 | CN | [p-OCH₃-C₆H₄-CO] | H | CH₃ | CH₃ | CH₃ | —CH₂CH(OCH₃)CH₂— | 2-OCH₃ | CN | [p-OCH₃-C₆H₄-CO] |
| 77 | CN | [thiophene-CO] | H | CH₃ | CH₃ | CH₃ | —CH₂CH(OCOC₂H₅)CH₂— | 3-Cl | CN | [thiophene-CO] |
| 78 | CN | COC(CH₃)₃ | H | CH₃ | CH₃ | CH₃ | —CH₂CH(OCH₃)CH₂— | 3-Br | CN | COC(CH₃)₃ |
| 79 | CN | SO₂C₆H₅ | H | CH₃ | CH₃ | CH₃ | —CH₂CH(C₆H₅)CH₂— | 3-F | CN | SO₂C₆H₅ |
| 80 | CN | CO₂C₂H₄CN | CH₃ | CH₃ | CH₃ | CH₃ | —CH₂CH₂— | 2-OCH₃ | CN | CO₂C₂H₄CN |
| 81 | CN | C₆H₅ | CH₃ | CH₃ | CH₃ | CH₃ | —CH₂CH₂— | 2-OCH₃ | CN | C₆H₅ |
| 82 | CN | [oxadiazole-CH₃] | H | H | H | H | —CH₂CH₂N(CH₃)CH₂CH₂— | 2-OCH₃ | CN | [oxadiazole-CH₃] |
| 83 | CN | [thiadiazole] | H | H | CH₃ | H | —CH₂CH₂O—C₆H₄—OCH₂CH₂— | | CN | [thiadiazole] |
| 84 | CN | CO₂C₆H₅ | H | CH₃ | CH₃ | CH₃ | —CH₂CH₂O—C₆H₄—OCH₂CH₂— | 2-OCH₃ | CN | CO₂C₆H₅ |

TABLE 2-continued

| Example No. | P | Q | (R)$_n$ | R$_3$ | R$_4$ | R$_5$ | R$_2$ | (R')$_n$ | P$^1$ | Q$^1$ |
|---|---|---|---|---|---|---|---|---|---|---|
| 85 | CN | CO$_2$CH$_2$C$_6$H$_5$ | CH$_3$ | H | H | H | —CH$_2$CH$_2$O—(thiophene ring)—OCH$_2$CH$_2$— | 2-OC$_2$H$_5$ | CN | CO$_2$CH$_2$C$_6$H$_5$ |
| 86 | CN | ![structure]($CO_2C_2H_4OCCH_3$, N=C-N-CH$_3$ with phenyl) | H | CH$_3$ | CH$_3$ | CH$_3$ | —CH$_2$CH$_2$— | 2,6-di-CH$_3$ | CN | ![structure]($CO_2C_2H_4OCCH_3$, N=C-N-CH$_3$ with phenyl) |
| 87 | CN | ![structure](O=C-N, C$_2$H$_4$OH with phenyl) | H | CH$_3$ | CH$_3$ | CH$_3$ | —CH$_2$CH$_2$— | H | CN | ![structure](O=C-N, C$_2$H$_4$OH with phenyl) |
| 88 | CN | ![structure](O=C-N, C$_2$H$_4$OH with phenyl) | CH$_3$ | CH$_3$ | CH$_3$ | CH$_3$ | —CH$_2$CH$_2$— | 2-OCH$_3$ | CN | ![structure](O=C-N, C$_2$H$_4$OH with phenyl) |
| 89 | CN | ![structure](O=C-NH with thiophene) | CH$_3$ | CH$_3$ | CH$_3$ | CH$_3$ | —CH$_2$CH$_2$— | 2-OCH$_3$ | CN | ![structure](O=C-NH with thiophene) |
| 90 | CN | O=COC$_2$H$_4$Cl | CH$_3$ | CH$_3$ | CH$_3$ | CH$_3$ | —CH$_2$CH$_2$— | 2-OCH$_3$ | CN | O=COC$_2$H$_4$Cl |

TABLE 3

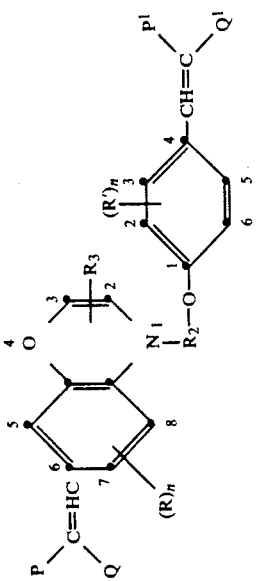

| Example No. | P | Q | (R)$_n$ | R$_3$ | R$_2$ | (R')$_n$ | P$^1$ | Q$^1$ |
|---|---|---|---|---|---|---|---|---|
| 91 | CN | CO$_2$CH$_3$ | H | H | —CH$_2$CH$_2$— | H | CN | CO$_2$CH$_3$ |
| 92 | CN | CO$_2$CH$_3$ | H | 2-CH$_3$ | —CH$_2$CH$_2$CH$_2$— | H | CN | CO$_2$CH$_3$ |
| 93 | CN | CO$_2$C$_2$H$_5$ | 7-CH$_3$ | H | —CH$_2$CH—CH$_2$— <br>               \|<br>              CH$_3$ | H | CN | CO$_2$C$_2$H$_5$ |
| 94 | CN | CO$_2$C$_2$H$_5$ | 7-CH$_3$ | 2-CH$_3$ | —CH$_2$CH$_2$— | 2-OCH$_3$ | CN | CO$_2$C$_2$H$_5$ |
| 95 | CN | CO$_2$C$_2$H$_5$ | 5-CH$_3$ | 2-CH$_3$ | —CH$_2$CH$_2$— | 2-OC$_2$H$_5$ | CN | CO$_2$C$_4$H$_{9-n}$ |
| 96 | CN | CO$_2$C$_4$H$_{9-n}$ | 8-CH$_3$ | 2-CH$_3$ | —CH$_2$CH$_2$OCH$_2$CH$_2$— | 2,6-di-CH$_3$ | CN | CO$_2$C$_2$H$_4$OH |
| 97 | CN | CO$_2$C$_2$H$_4$OH | H | H | —CH$_2$CH$_2$N(SO$_2$CH$_3$)CH$_2$CH$_2$— | | | |
| 98 | CN | ⟨N=C-O benzisoxazole⟩ | 7-CH$_3$ | 2-CH$_3$ | —CH$_2$CH$_2$CH$_2$— | 3,5-di-CH$_3$ | CN | ⟨N=C-O benzisoxazole⟩ |
| 99 | CO$_2$C$_2$H$_5$ | ⟨N=C-O benzisoxazole⟩ | | | —CH$_2$CH$_2$SCH$_2$CH$_2$— | 3-CH$_3$ | CO$_2$C$_2$H$_5$ | ⟨N=C-O benzisoxazole⟩ |
| 100 | CN | CN | 7-CH$_3$ | 2-CH$_3$ | —CH$_2$CH$_2$— | 2-OCH$_3$ | CN | CN |
| 101 | CN | SO$_2$CH$_3$ | 7-CH$_3$ | 2-CH$_3$ | —CH$_2$CH$_2$— | 2-OCH$_3$ | CN | CO$_2$C$_6$H$_5$ |
| 102 | CN | SO$_2$C$_6$H$_5$ | 7-CH$_3$ | 2,3-di-CH$_3$ | —CH$_2$CH(OH)CH$_2$— | 2-OCH$_3$ | CN | SO$_2$C$_6$H$_5$ |
| 103 | CN | O=CNH$_2$ | 7-CH$_3$ | 3-CH$_3$ | —CH$_2$CH(OCCH$_3$)CH$_2$— <br>                 ||<br>                O | 3-Cl | CN | O=CNH$_2$ |

TABLE 3-continued
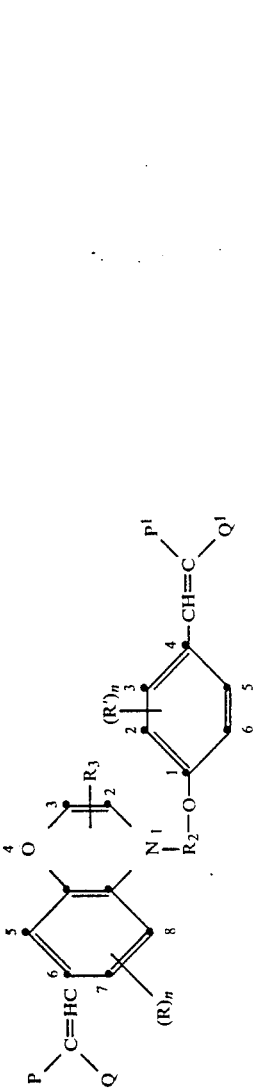
| Example No. | P | Q | (R)n | R3 | R2 | (R')n | P1 | Q1 |
|---|---|---|---|---|---|---|---|---|
| 104 | CN | CO2CH3 | 7-CH3 | 2-CH3 | —CH2CHCH2— (with 3-methoxyphenoxy group: CH2 attached to O-C6H3-OCH3) with substituent —C(CN)=CH- CO2CH3 | 2-OCH3 | CN | CO2CH3 |
| 105 | CN | 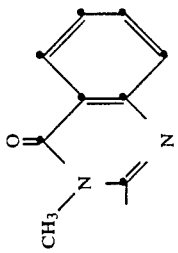 | 7-CH3 | 2-CH3 | —CH2CH2— | 2-OCH3 | CN | 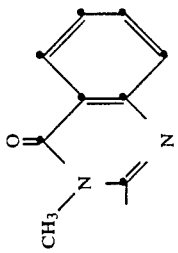 |
| 106 | CN | 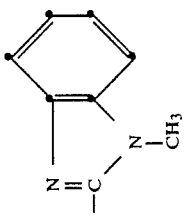 | 7-CH3 | 2-CH3 | —CH2CH(OCH3)CH2— | 2-Cl | CN | 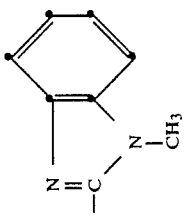 |
| 107 | CN | 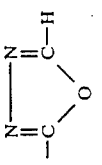 | 7-CH3 | H | —CH2CH(C6H5)CH2— | 2-OCH3 | CN | 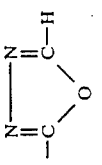 |
| 108 | CO2CH3 | CO2CH3 | 7-CH3 | 2-CH3 | —CH2CH(Cl)CH2— | 2-OC4H9—n | CO2CH3 | CO2CH3 |

TABLE 3-continued

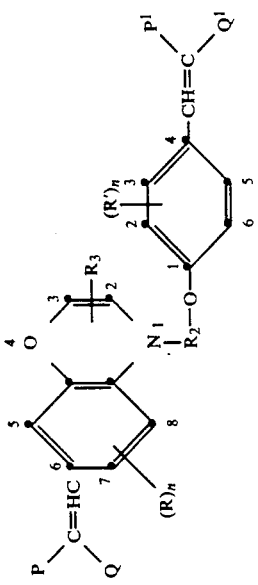

| Example No. | P | Q | (R)$_n$ | R$_3$ | R$_2$ | (R')$_n$ | P$^1$ | Q$^1$ |
|---|---|---|---|---|---|---|---|---|
| 109 | CN | (quinoline) | 7-CH$_3$ | 2-CH$_3$ | —CH$_2$CH$_2$CH$_2$CH$_2$— | 2-OCH$_3$ | CN | (quinoline) |
| 110 | CN | (pyrimidine) | 7-CH$_3$ | 2-CH$_3$ | —CH$_2$CH$_2$— | 2-OCH$_3$ | CN | (pyrimidine) |
| 111 | CN | 4-NO$_2$-C$_6$H$_4$-CO— | 7-CH$_3$ | H | CH$_3$ / —CH$_2$CH$_2$NCH$_2$— | 2-OCH$_3$ | CN | 4-NO$_2$-C$_6$H$_4$-CO— |
| 112 | CN | 4-OCH$_3$-C$_6$H$_4$-CO— | 7-CH$_3$ | 2-CH$_3$ | C$_6$H$_5$ / —CH$_2$CH$_2$NCH$_2$— | 2-OCH$_3$ | CN | 4-OCH$_3$-C$_6$H$_4$-CO— |
| 113 | CN | (thiophene-CONH—) | 7-CH$_3$ | 2-CH$_3$ | COC$_6$H$_5$ / —CH$_2$CH$_2$NCH$_2$— | 2-OCH$_3$ | CN | (thiophene-CONH—) |

TABLE 3-continued

| Example No. | P | Q | (R)$_n$ | R$_3$ | R$_2$ | (R')$_n$ | P$^1$ | Q$^1$ |
|---|---|---|---|---|---|---|---|---|
| 114 | CN | -C(=O)NH-C$_6$H$_4$-CH$_2$OH | 7-CH$_3$ | 2-CH$_3$ | -CH$_2$CH$_2$- | 2-OCH$_3$ | CN | -C(=O)NH-C$_6$H$_4$-CH$_2$OH |
| 115 | CN | -C(=O)NHC$_2$H$_4$OH | 7-CH$_3$ | 2-CH$_3$ | -CH$_2$CH$_2$- | 2-OCH$_3$ | CN | -C(=O)NHC$_2$H$_4$OH |
| 116 | CN | -C(=O)-N(CH$_3$)-CH$_2$CH$_2$OH | 7-CH$_3$ | 2-CH$_3$ | -CH$_2$CH$_2$- | 2-OCH$_3$ | CN | -C(=O)-N(CH$_3$)-C$_2$H$_4$OH |
| 117 | CN | -C(=O)-N(C$_6$H$_5$)-C$_2$H$_4$OH | 7-CH$_3$ | 2-CH$_3$ | -CH$_2$CH$_2$- | 2-OCH$_3$ | CN | -C(=O)-N(C$_6$H$_5$)-C$_2$H$_4$OH |
| 118 | CN | -CO$_2$CH$_2$-(furyl) | 7-CH$_3$ | 2-CH$_3$ | -CH$_2$CH$_2$- | 2-OCH$_3$ | CN | -CO$_2$CH$_2$-(furyl) |

TABLE 4

Structure shown with positions: a bicyclic system with C=HC-P/Q on one ring, (R)n substituent, R2 linker to O-phenyl ring bearing (R')n and CH=C(P¹)(Q¹).

| Example No. | P | Q | (R)n | (R)3 | R4 | R5 | R2 | (R')n | P¹ | Q¹ |
|---|---|---|---|---|---|---|---|---|---|---|
| 119 | CN | $CO_2CH_3$ | H | $CH_3$ | $CH_3$ | $CH_3$ | $-CH_2CH_2-$ | H | CN | $CO_2CH_3$ |
| 120 | CN | $CO_2C_2H_5$ | H | H | H | H | $-CH_2CH_2-$ | 2-$OCH_3$ | CN | $CO_2C_2H_5$ |
| 121 | CN | $CO_2CH_3$ | 6-$CH_3$ | $CH_3$ | H | H | $-CH_2CH_2OCH_2CH_2-$ | H | CN | $CO_2CH_3$ |
| 122 | CN | $CO_2CH_3$ | 6-$CH_3$ | H | H | H | $-CH_2CH_2SCH_2CH_2-$ | H | CN | $CO_2CH_3$ |
| 123 | CN | CN | 6-$OCH_3$ | H | H | H | $-CH_2CH_2CH_2-$ | 2-$OC_2H_5$ | CN | $CO_2CH_3$ |
| 124 | CN | CN | 6-$OCH_3$ | H | H | H | $-CH_2CH(CH_3)CH_2-$ | 2-$OC_4H_9$-n | CN | CN |
| 125 | CN | (2-Cl, 6-substituted phenyl with N=C-O ring) | 6-$CH_3$ | H | H | H | $-CH_2CH_2CH_2-$ | 2-$OCH_3$ | CN | (2-Cl, 6-substituted phenyl with N=C-O ring) |
| 126 | CN | $CO_2CH(CH_3)_2$ | H | H | H | H | $-CH_2CH(OH)CH_2-$ | 2-$OCH_2$ | CN | $CO_2CH(CH_3)_2$ |
| 127 | CN | $CO_2C_2H_4OCH_3$ | H | $CH_3$ | H | H | $-CH_2CH_2-$ | 2-$OCH_3$ | CN | $CO_2C_2H_4OCH_3$ |
| 128 | CN | $SO_2CH_3$ | H | H | H | H | $-CH_2CH(OCCH_3)CH_2-$ (with =O) | 3-$CH_3$ | CN | $SO_2CH_3$ |
| 129 | CN | (3,4-diCl-phenyl-$SO_2$) | H | | | | $-CH_2CH_2NCH_2CH_2-$ (with $SO_2C_2H_5$) | 3,5-di-$CH_3$ | CN | (3,4-diCl-phenyl-$SO_2$) |
| 130 | $CO_2CH_3$ | $CO_2CH_3$ | 6-$CH_3$ | $CH_3$ | H | H | $-CH_2CH_2-$ (p-xylylene) | 2,6-di-$CH_3$ | $CO_2CH_3$ | $CO_2CH_3$ |
| 131 | CN | $CO_2H$ | 6-Cl | $CH_3$ | H | H | (p-xylylene $-CH_2-C_6H_4-CH_2-$) | 3-$CH_3$ | CN | $CO_2H$ |

TABLE 4-continued

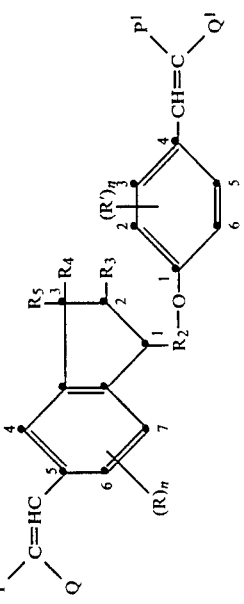

| Example No. | P | Q | (R)$_n$ | (R)$_3$ | R$_4$ | R$_5$ | R$_2$ | (R')$_n$ | P$^1$ | Q$^1$ |
|---|---|---|---|---|---|---|---|---|---|---|
| 132 | CN | $\underset{\underset{O}{\parallel}}{C}$NHC$_2$H$_4$OH | H | CH$_3$ | H | H | —CH$_2$— (with S ring, CH$_2$) | H | CN | $\underset{\underset{O}{\parallel}}{C}$NHC$_2$H$_4$OH |
| 133 | CO$_2$C$_2$H$_5$ | (phenyl with N=C—O) | H | CH$_3$ | CH$_3$ | CH$_3$ | —CH$_2$CH$_2$O— (phenyl with OCH$_2$Cl$_2$) | H | CO$_2$C$_2$H$_5$ | (phenyl with N=C—O) |
| 134 | CN | —CO— (phenyl) | H | H | H | H | —CH$_2$CH$_2$NCH$_2$CH$_2$— (CH$_3$) | H | CN | —CO— (phenyl) |
| 135 | CN | —CONH— (phenyl with Cl) | H | H | H | H | —CH$_2$CH$_2$— | H | CN | —CONH— (phenyl with CH$_2$OH) |
| 136 | CN | (furanone O=C—O) | H | H, H | H | H | —CH$_2$CH$_2$— | H | CN | (furanone O=C—O) |

TABLE 4-continued
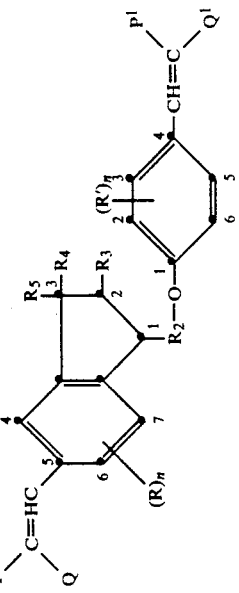
| Example No. | P | Q | (R)n | (R)3 | R4 | R5 | R2 | (R')n | P1 | Q1 |
|---|---|---|---|---|---|---|---|---|---|---|
| 137 | CN | O=C-N(CH3)(C2H4OH) | 6-CH3 | CH3 | CH3 | CH3 | —CH2CH2— | 2-OCH3 | CN | O=C-N(CH3)(C2H4OH) |
| 138 | CN | O=C-N(C2H4OH)(4-CH3-C6H4) | 4-CH3 | CH3 | CH3 | CH3 | —CH2CH2— | 2-OCH3 | CN | O=C-N(C2H4OH)(4-CH3-C6H4) |
| 139 | CN | O=COCH2-(2-thienyl) | 7-CH3 | CH3 | H | H | —CH2CH(C6H5)CH2— | 2-OCH3 | CN | O=COCH2-(2-thienyl) |
| 140 | CH | O=COC2H4CN | 6-CH3 | CH3 | H | H | —CH2CH2— | 2-OCH3 | CN | O=COC2H4CN |
| 141 | CN | O=COC2H4OCH3 | 6-CH3 | CH3 | H | H | —CH2CH2— | 2-OCH3 | CN | O=COC2H4OCH3 |
| 142 | CN | N=C-NH-(benzo) | 6-CH3 | H | H | H | —CH2CH2— | 2-OCH3 | CN | N=C-NH-(benzo) |

TABLE 4-continued
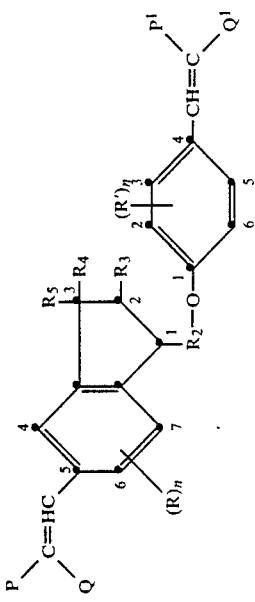
| Example No. | P | Q | (R)ₙ | (R)₃ | R₄ | R₅ | R₂ | (R')ₙ | P¹ | Q¹ |
|---|---|---|---|---|---|---|---|---|---|---|
| 143 | CN | CO₂CH₃ | 6-CH₃ | H | H | H | —CH₂CHCH₂— | 2-OCH₃ | CN | CO₂CH₃ |

TABLE 5

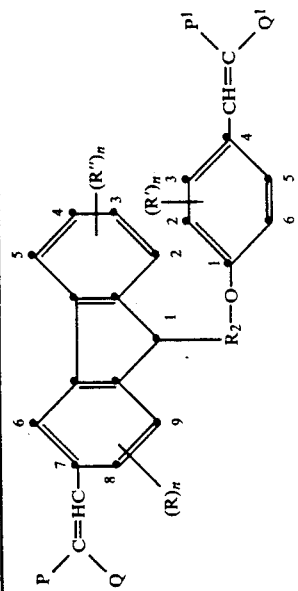

| Example No. | P | Q | (R)n | R2 | (R'')n | (R')n | P1 | Q1 |
|---|---|---|---|---|---|---|---|---|
| 144 | CN | CO2CH3 | H | —CH2CH2— | H | H | CN | CO2CH3 |
| 145 | CN | CO2CH3 | H | —CH2CH2CH2— | H | 2-OCH3 | CN | CO2CH3 |
| 146 | CN | CN | H | —CH2CH2— | H | 2-OCH3 | CN | CN |
| 147 | CN | CN | H | —CH2CH2CH2CH2— | H | 2-OCH3 | CN | CO2CH3 |
| 148 | CN | CO2CH3 | 8-CH3 | —CH2CH2— | 4-CH3 | 2-OCH3 | CN | CO2CH3 |
| 149 | CN | C6H4-CO2CH2 (phenyl) | 8-CH3 | —CH2CH2OCH2CH2— | H | H | CN | C6H4-CO2CH2 (phenyl) |
| 150 | CN | CO2C2H4OH | 6,8-di-CH3 | —CH2CH2SCH2CH2— | H | 2-OCH3 | CN | CO2C2H4OH |
| 151 | CN | CO2C2H4Cl | 6,9-di-CH3 | —CH2CH2SO2CH2CH2— | H | 2-OCH3 | CN | CO2C2H4Cl |
| 152 | CN | CO2C2H4CN | 8-CH3 | —CH2CH2— | 4-OCH3 | 2-OCH3 | CN | CO2C2H4CN |
| 153 | CN | CO2C2H4OC2H5 | 8-CH3 | —CH2CH2— | 3,4-di-Cl | H | CN | CO2C2H4OC2H5 |
| 154 | CN | thiophene-CO2CH2 | 8-CH3 | —CH2CH(OH)CH2— | 4-Br | 2-CH3 | CN | thiophene-CO2CH2 |
| 155 | CN | Cl-phenyl-N=C-O | H | —CH2CH2— | H | 2-OCH3 | CN | Cl-phenyl-N=C-O |

TABLE 5-continued

| Example No. | P | Q | (R)$_n$ | R$_2$ | (R'')$_n$ | (R')$_n$ | P$^1$ | Q$^1$ |
|---|---|---|---|---|---|---|---|---|
| 156 | CO$_2$C$_2$H$_5$ | (isoxazolone ring) | 9-CH$_3$ | —CH$_2$CH$_2$— | H | 3-CH$_3$ | CO$_2$C$_2$H$_5$ | (isoxazolone ring) |
| 157 | CO$_2$C$_2$H$_5$ | CO$_2$C$_2$H$_5$ | H | —CH$_2$CH$_2$— | H | 2-OCH$_3$ | CO$_2$C$_2$H$_5$ | CO$_2$C$_2$H$_5$ |
| 158 | CN | CO$_2$C$_2$H$_5$ | H | —CH$_2$CH$_2$— | H | 2-OCH$_3$ | CO$_2$C$_2$H$_5$ | CO$_2$C$_2$H$_5$ |
| 159 | CN | CNHC$_2$H$_4$OH (O=) | H | —CH$_2$CH(OCCH$_3$)CH$_2$—  (O=) | H | 3,5-di-CH$_3$ | CN | CNHC$_2$H$_4$OH (O=) |
| 160 | CN | (O=)C(CH$_3$)N(C$_2$H$_4$OH) | H | C$_6$H$_5$ —CH$_2$CHCH$_2$— | H | 2,6-di-CH$_3$ | CN | (O=)C(CH$_3$)N(C$_2$H$_4$OH) |
| 161 | CN | CO$_2$CH$_3$ | H | —CH$_2$CH$_2$— (phenyl-O— with CN,CO$_2$CH$_3$ vinyl) | H | H | CN | CO$_2$CH$_3$ |
| 162 | CN | SO$_2$CH$_3$ | H | —CH$_2$CH(OH)CH$_2$— SO$_2$CH$_3$ | H | H | CN | SO$_2$CH$_3$ |
| 163 | CN | (4-Cl-C$_6$H$_4$-SO$_2$-) | H | —CH$_2$CHNCH$_2$CH$_2$— | H | H | CN | (4-Cl-C$_6$H$_4$-SO$_2$-) |

TABLE 5-continued
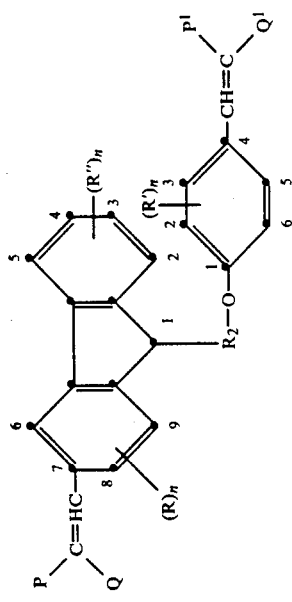
| Example No. | P | Q | (R)ₙ | R₂ | (R″)ₙ | (R′)ₙ | P¹ | Q¹ |
|---|---|---|---|---|---|---|---|---|
| 164 | CN | (4-methoxyphenyl C=O) | H | -CH₂CH₂NCH₂CH₂- with CH₃ | H | H | CN | (4-methoxyphenyl C=O) |
| 165 | CN | (o-acylaminophenyl) | H | -CH₂CH₂- | H | H | CN | (o-acylaminophenyl) |
| 166 | CN | (phenyl-NHC=O) | H | -CH₂CH₂- | H | H | CN | (phenyl-NHC=O) |
| 167 | CN | (CH₂OH-phenyl-NHC=O) | H | -CH₂CH₂- | H | H | CN | (CH₂OH-phenyl-NHC=O) |

TABLE 5-continued

| Example No. | P | Q | (R)n | R2 | (R'')n | (R')n | P1 | Q1 |
|---|---|---|---|---|---|---|---|---|
| 168 | CN | —COCH₂—(furan ring with O) | H | —CH₂CH₂— | H | H | CN | —COCH₂—(furan ring with O) |
| 169 | CN | —CNH—(thiopyran ring with S) | H | —CH₂CH₂— | H | H | CN | —CNH—(thiopyran ring with S) |
| 170 | CN | (oxadiazole ring N=CH, N=C, O) | H | —CH₂CH₂— | H | H | CN | (oxadiazole ring N=CH, N=C, O) |

TABLE 6

| Examples No. | P | Q | (R)$_n$ | R$_2$ | (R'')$_n$ | (R')$_n$ | P$^1$ | Q$^1$ |
|---|---|---|---|---|---|---|---|---|
| 171 | CN | CO$_2$CH$_3$ | H | —CH$_2$CH$_2$— | H | H | CN | CO$_2$CH$_3$ |
| 172 | CN | CO$_2$C$_2$H$_5$ | H | —CH$_2$CH$_2$CH$_2$— | H | 2-OCH$_3$ | CN | CO$_2$CH$_3$ |
| 173 | CN | CN | H | —CH$_2$CH$_2$CH$_2$— | H | 2-OCH$_3$ | CN | CO$_2$C$_2$H$_5$ |
| 174 | CN | CN | H | —CH$_2$CH$_2$— | H | H | CN | CN |
| 175 | CN | CO$_2$CH$_3$ | 8-CH$_3$ | —CH$_2$CH$_2$— | H | H | CN | CO$_2$CH$_3$ |
| 176 | CN | CO$_2$CH$_3$ | 8-CH$_3$ | —CH$_3$<br>—CH$_2$CHCH$_2$— | 5-CH$_3$ | 2-OCH$_3$ | CN | CO$_2$CH$_3$ |
| 177 | CN | CO$_2$C$_4$H$_9-n$ | 8-CH$_3$ | —CH$_2$CH(OH)CH$_2$— | 4-Cl | 2-OC$_4$H$_{9-n}$ | CN | CO$_2$C$_4$H$_{9-n}$ |
| 178 | CN | CO$_2$C$_2$H$_4$OH | H | —CH$_2$OH(OC$_2$H$_5$)CH$_2$— | 3-CH$_3$ | 2-OCH$_3$ | CN | CO$_2$C$_2$H$_4$OH |
| 179 | CN | CO$_2$C$_2$H$_4$OCH$_3$ | H | ![169 phenyl] | 3-OCH$_3$ | 2-CH$_3$ | CN | CO$_2$C$_2$H$_4$OCH$_3$ |
| 180 | CN | CO$_2$C$_2$H$_4$OH | H | —CH$_2$—C$_6$H$_4$—CH$_2$— | 2-Cl | 3,5-di-CH$_3$ | CN | CO$_2$C$_2$H$_4$OH |
| 181 | CN | CO$_2$C$_2$H$_4$Cl | H | —CH$_2$—(thiophene)—CH$_2$— | H | H | CN | CO$_2$C$_2$H$_4$Cl |
| 182 | CN | $\overset{O}{\underset{\|}{C}}$NHC$_2$H$_4$OH | 7-CH$_3$ | —CH$_2$CH$_2$CH$_3$ | 2-OCH$_3$ | CN | $\overset{O}{\underset{\|}{C}}$NHC$_2$H$_4$OH | |

TABLE 6-continued

| Examples No. | P | Q | (R)n | R2 | (R")n | (R')n | P¹ | Q¹ |
|---|---|---|---|---|---|---|---|---|
| 183 | CN | [2-Cl-benzisoxazol-3-yl (N=C-O)] | H | —CH₂CH₂OCH₂CH₂CH₂— | H | 2-OCH₃ | CN | [2-Cl-benzisoxazol-3-yl (N=C-O)] |
| 184 | CO₂C₂H₅ | CO₂C₂H₅ | H | —CH₂CH₂— | H | 2-OCH₃ | CO₂C₂H₅ | CO₂C₂H₅ |
| 185 | CN | CN | H | —CH₂CH₂— | H | 2-OCH₃ | CN | CN |
| 186 | CO₂C₂H₅ | CO₂C₂H₅ | H | —CH₂CH₂— | H | 2-OCH₃ | CO₂C₂H₅ | CO₂C₂H₅ |
| 187 | CN | CN | H | —CH₂CH₂NCH₂CH₂— (N–SO₂C₂H₅) | H | 2,6-di-CH₃ | CN | CN |
| 188 | CN | [4-Cl-C₆H₄–C(=O)–] | H | —CH₂CH₂NCH₂CH₂— (N–SO₂-p-tolyl) | H | 3-Cl | CN | [4-Cl-C₆H₄–C(=O)–] |

TABLE 6-continued
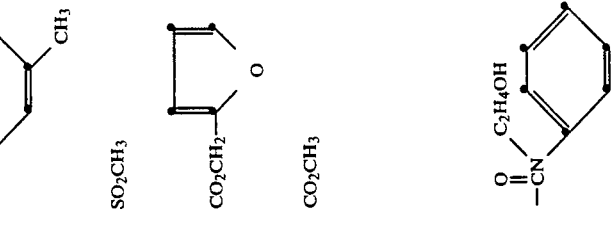
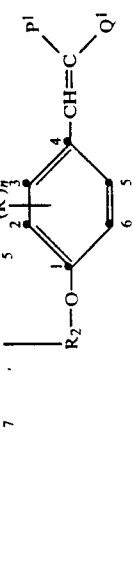
| Examples No. | P | Q | (R)ₙ | R₂ | (R'')ₙ | (R')ₙ | P¹ | Q¹ |
|---|---|---|---|---|---|---|---|---|
| 189 | CN | ![3-CH₃-phenyl-SO₂] | H | —CH₂CH(OCCH₃)CH₂—  (O=) | H | 2-OCH₃ | CN | ![3-CH₃-phenyl-SO₂] |
| 190 | CO₂C₂H₅ | SO₂CH₃ | H | —CH₂CH₂SCH₂CH₂— | H | H | CO₂C₂H₅ | SO₂CH₃ |
| 191 | CN | ![furan-CO₂CH₂] | H | ![p-OCH₂CH₃-phenyl-CH₂O—] | H | H | CN | ![furan-CO₂CH₂] |
| 192 | CN | CO₂CH₃ | H | ![CH₂CH=C(CN)(CO₂CH₃) on OCH₃-phenyl-CH₂O—] | H | 2-OCH₃ | CN | CO₂CH₃ |
| 193 | CN | ![phenyl-C(=O)-N(C₂H₄OH)] | H | —CH₂CH₂— | H | 2-OCH₃ | CN | ![phenyl-C(=O)-N(C₂H₄OH)] |

TABLE 6-continued
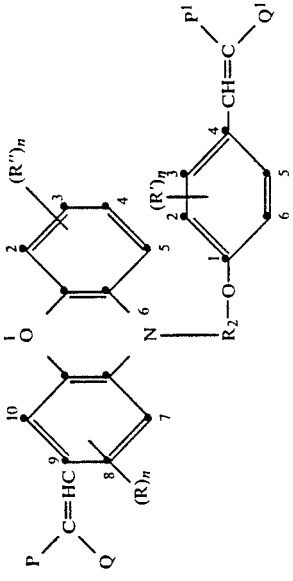
| Examples No. | P | Q | (R)ₙ | R₂ | (R'')ₙ | (R')ₙ | P¹ | Q¹ |
|---|---|---|---|---|---|---|---|---|
| 194 | CN | | H | —CH₂CH₂— | H | H | CN | |
| 195 | CN | O=CN(C₂H₄OH)₂ | H | —CH₂CH₂— | H | H | CN | CN |
| 196 | CN | ![](oxazoline ring N=CH-O-C=N) | H | —CH₂CH(OH)CH₂— | H | H | CN | ![](oxazoline ring N=CH-O-C=N) |

The invention has been described in detail with particular reference to preferred embodiments thereof, but it will be understood that variations and modifications can be effected within the spirit and scope of the invention.

We claim:

1. A polymeric composition comprising a molding or fiber grade condensation polymer having in the range of about 1.0 up to 100,000 ppm of the reactant residue moieties of one or more bis- and tris-methine compounds having the structural formula

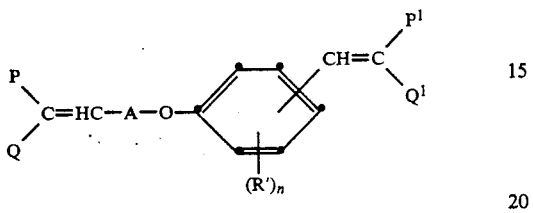

wherein
A is selected from the radicals

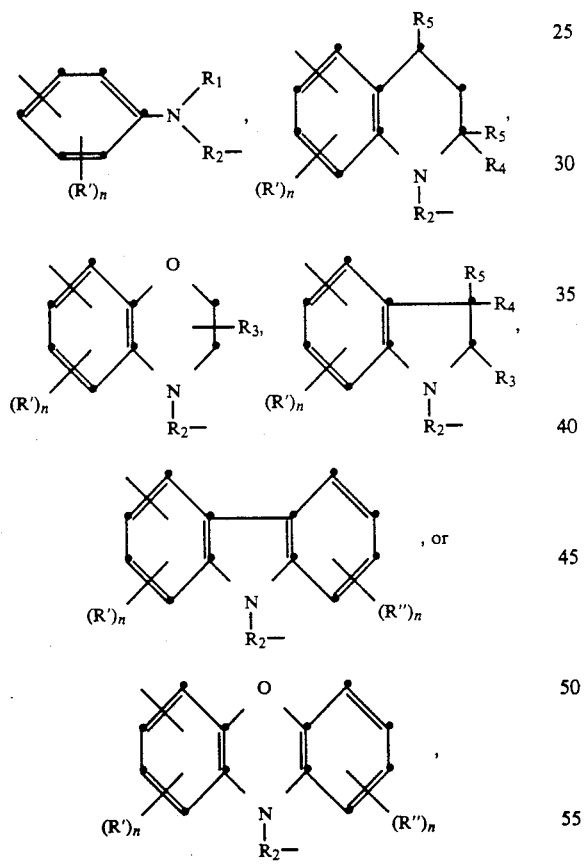

wherein
R' and R" are each selected from chlorine, bromine, fluorine, alkyl, alkoxy, phenyl, phenoxy, and phenylthio;
n is 0, 1, or 2;
$R_1$ is selected from cycloalkyl; cycloalkyl substituted with one or two or alkyl, —OH, alkoxy, halogen, or hydroxy substituted alkyl; phenyl; phenyl substituted with alkyl, alkoxy, halogen, alkanoylamino, carboxy, cyano, or alkoxycarbonyl; straight or branched lower alkenyl; straight or branched alkyl of 1-8 carbons and such alkyl substituted with the following: hydroxy; halogen; cyano; succinimido; hydroxysuccinimido; acyloxysuccinimido; glutarimido; phenylcarbamoyloxy; phthalimido; 4-carboxyphthalimido; phthalimidino; 2-pyrrolidono; cyclohexyl; phenyl; phenyl substituted with alkyl, alkoxy, halogen, hydroxy alkanoylamino, carboxy, cyano, or alkoxycarbonyl; alkylsulfonyl; vinylsulfonyl; acrylamido; sulfamyl; benzoylsulfonicimido; alkylsulfonamido; phenylsulfonamido; alkoxycarbonylamino; alkylcarbamoyloxy; groups of the formula

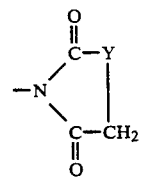

wherein Y is —NH—,

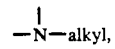

—O—, —S—, or —CH$_2$O; —S—R$_6$; SO$_2$CH$_2$CH$_2$SR$_6$; wherein R$_6$ is alkyl, phenyl, phenyl substituted with halogen, alkyl, alkoxy, alkanoylamino, cyano, or alkoxycarbonyl; pyridyl; pyrimidinyl; benzoxazolyl; benzimidazolyl; benzothiazolyl; radicals of the formula

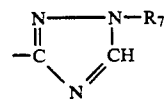

—OXR$_8$; —NHXR$_8$; —X—R$_8$; —CONR$_7$R$_7$; and —SO$_2$NR$_7$R$_7$; wherein R$_7$ is selected from H, aryl, alkyl, and alkyl substituted with halogen, —OH, phenoxy, aryl, —CN, cycloalkyl, alkylsulfonyl, alkylthio, alkanoyloxy, or alkoxy; X is —CO—, —COO—, or —SO$_2$—; R$_8$ is selected from alkyl and alkyl substituted with halogen, hydroxy, phenoxy, aryl, cyano, cycloalkyl, alkylsulfonyl, alkylthio, alkanoyloxy, and alkoxy; and when X is —CO—, R$_8$ also can be hydrogen, amino, alkenyl, alkylamino, dialkylamino, arylamino, aryl, or furyl; alkoxy; alkoxy substituted with hydroxy, cyano, alkanoyloxy, or alkoxy, phenoxy; phenoxy substituted with one or more of alkyl, carboxy, alkoxy, carbalkoxy, or halogen; R$_1$ can also be —R$_2$-Z—B—CH=C(P)Q wherein Z is O or S, and B is arylene;

R$_2$ is alkylene; alkylene substituted with alkoxy, aryl, aryloxy, halogen, hydroxy, acyloxy, cyano, and —R$_2$—Z—B—CH=C(P)Q; arylene, aralkylene, alkylene-O-alkylene; alkylene-O-arylene-O-alkylene; alkylene-arylene-alkylene; alkylene-C$_6$-H$_{10}$-alkylene; alkylene-S-alkylene; alkylene-SO$_2$-alkylene;

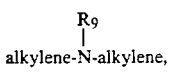

wherein $R_9$ is alkyl, aryl, alkanoyl, alkylsulfonyl, aroyl, or arylsulfonyl;

$R_3$, $R_4$, and $R_5$ are each selected from hydrogen and alkyl;

P and Q and $P^1$ and $Q^1$ are selected from cyano, carbalkoxy, carbaryloxy, carbaralkyloxy, carbalkenyloxy, carbamyl, carboxy, acyl, aroyl, N-alkylcarbamyl, N-alkyl-N-arylcarbamyl, N,N-dialkylcarbamyl, N-arylcarbamyl, N-cyclohexylcarbamyl, aryl, 2-benzoxazolyl, 2-benzothiazolyl, 2-benzimidazolyl, 1,3,4-thiadialzol-2-yl, 1,3,4-oxadiazol-2-yl, $SO_2$ alkyl, $SO_2$ aryl, pyridyl, pyrolyl, quinolyl, pyrimidyl and

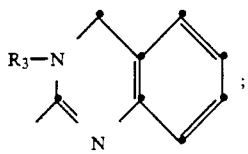

wherein:

in the above definitions, each alkyl, alkoxy, aryl, or cycloalkyl moiety or portion of a group or radical may be substituted where appropriate with hydroxyl, acyloxy, alkyl, cyano, alkoxycarbonyl, halogen, alkoxy, aryl, aryloxy, or cycloalkyl;

each methine compound, preferably at least one of A, P, Q, $P^1$ or $Q^1$ thereof, bears a group capable of reacting under polymerization conditions, to incorporate the multichromophoric compound into the polymer, including the following: carboxy, carbalkoxy, carbaryloxy, N-alkylcarbamyloxy, acyloxy, chlorocarbonyl, carbamyloxy, N-alkylcarbamyloxy, amino, alkylamino, hydroxyl, N-phenylcarbamyloxy, cyclohexanoyloxy, and carbocyclohexyloxy, wherein the alkyl and/or aryl groups may contain common substituents such as hydroxyl, cyano, acyloxy, carbalkoxy, phenyl, and halogen which do not interfere with the condensation reaction, and in all of the above definitions the alkyl or alkylene moieties or portions of the various groups contain 1-8 carbon atoms, straight or branched chain.

2. The composition of claim 1 wherein said bis- and tris-methine compounds are present in an amount ranging from about 1.0 up to 50,000 ppm.

3. The composition of claim 1 wherein said bis- and tris-methine compounds are present in an amount ranging from about 2.0 up to 1,500 ppm.

4. The composition of claim 1 wherein the polymer is a linear polyester, the acid moiety of which is comprised of at least about 50 mol % terephthalic acid, and the glycol moiety of which is comprised of at least about 50 mol % ethylene glycol or 1,4-cyclohexanedimethanol.

5. The composition of claim 1 wherein the polymer is an unsaturated, curable polyester comprised of at least one diol selected from the group consisting of propylene glycol, neopentyl glycol, ethylene glycol, 1,4-cyclohexanedimethanol, diethylene glycol, 2,2-dimethyl-1,3-propanediol, and 2,2,4-trimethyl-1,3-pentanediol, as well as mixtures of any two or more thereof, and at least one diacid selected from the group consisting of maleic acid, fumaric acid, and mixtures thereof with up to about 75 mol % based on the moles of acid, of phthalic or isophthalic acid.

6. A formed article of a composition of claim 1.

* * * * *